United States Patent
Liu et al.

(10) Patent No.: US 9,737,517 B2
(45) Date of Patent: Aug. 22, 2017

(54) PHARMACEUTICAL USE OF HEXAHYDRO-DIBENZO[A,G]QUINOLIZINE COMPOUNDS

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Xin Xie, Shanghai (CN); Haifeng Sun, Shanghai (CN); Jing Li, Shanghai (CN); Fei Zhao, Shanghai (CN); Ying Chen, Shanghai (CN); Zeng Li, Shanghai (CN); Yu Zhou, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 14/888,797

(22) PCT Filed: May 4, 2014

(86) PCT No.: PCT/CN2014/076743
§ 371 (c)(1),
(2) Date: Mar. 15, 2016

(87) PCT Pub. No.: WO2014/177065
PCT Pub. Date: Nov. 6, 2014

(65) Prior Publication Data
US 2016/0193195 A1    Jul. 7, 2016

(30) Foreign Application Priority Data

May 3, 2013 (CN) .......................... 2013 1 0161512

(51) Int. Cl.
*A61K 31/4375* (2006.01)

(52) U.S. Cl.
CPC .................. *A61K 31/4375* (2013.01)

(58) Field of Classification Search
CPC ..................................... A61K 31/4375
See application file for complete search history.

(56) References Cited

FOREIGN PATENT DOCUMENTS

CN    102526305 A    7/2012

OTHER PUBLICATIONS

Guh et al. European Journal of Pharmacology, (1999), 374, p. 503-510.*
Schafer et al. Drug Discovery Today, 2008, 13 (21/22), 913-916.*
Horig et al. Journal of Translational Medicine 2004, 2(44), p. 1-8.*
Wang et al. Yakugaku Zasshi, (2010), 130(9), p. 1207-1214.*
Guh et al., "Investigation of the effects of some alkaloidal a1-adrenoceptor antagonists on human hyperplastic prostate," European Journal of Pharmacology, vol. 374, pp. 503-510 (1999).

* cited by examiner

*Primary Examiner* — Yong Chu
(74) *Attorney, Agent, or Firm* — Panitch Schwarze Belisario & Nadel LLP

(57) ABSTRACT

Use of hexahydro-dibenzo[a,g]quinolizine compounds as shown in formula(I) in preparing a medicine for treating and/or preventing benign prostate hyperplasia diseases.

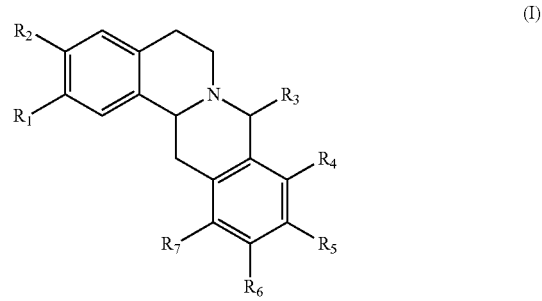

(I)

13 Claims, 3 Drawing Sheets

Inspection and grouping of BPH model rats

Compound efficacy verification

PHARMACEUTICAL USE OF HEXAHYDRO-DIBENZO[A,G]QUINOLIZINE COMPOUNDS

CROSS REFERENCE TO RELATED APPLICATION

This application is a Section 371 of International Application No. PCT/CN2014/076743, filed May 4, 2014, which was published in the Chinese language on Nov. 6, 2014, under International Publication No. WO 2014/177065 A1 and the disclosure of which is herein incorporated by reference in its entirety.

TECHNICAL FIELD

The present invention relates to field of pharmaceutical use of hexahydrodibenzo[a,g]quinolizine compound, and particularly to use of hexahydrodibenzo[a,g]quinolizine compound in preparing medicine for treating and/or preventing benign prostatic hyperplasia diseases.

BACKGROUND ART

Benign prostatic hyperplasia (BPH) is a physiological disease common in middle-aged and elderly men. Along with the inevitable aging population, the incidence of BPH grows significantly than that in the past, and BPH has become one of the most common diseases of middle-aged and elderly men in China. Statistics show that prostate hyperplasia morbidity is very low before age 40, about half suffer from benign prostatic hyperplasia in men over the age of 50, and nearly 90% of 80-year-old males suffer from this disease. Benign prostatic hyperplasia is a benign adenomatous hyperplasia of prostatic urethra surrounding area cells, and the progressive enlargement of gland causes prostate urethra structure and causes urinary bladder outflow obstruction. Initial clinical manifestation is lower urinary tract symptoms (LUTS), and it eventually may develop into urinary retention, bladder infections, bladder stones and kidney failure, and even endangers patient's life. Therefore, benign prostatic hyperplasia, as one of common diseases in middle-aged and elderly men in China and abroad, greatly reduces life quality of patients.

The pathogenesis of benign prostatic hyperplasia is very complicated, and relates to various enzymes and receptors. Currently, two drugs most widely used for treatment of BPH in clinical are 5α-reductase inhibitors and $\alpha_1$-adrenergic receptors antagonists, whose treatment respectively aims at prostate volume and smooth muscle tension which are two factors causing symptoms of benign prostatic hyperplasia. The 5α-reductase inhibitors reduce prostate volume and improve dysuria through inhibiting conversion of testosterone to dihydrotestosterone in body, thereby reducing content of dihydrotestosterone in the prostate. But these drugs are only suitable for treating BPH patients with increased prostate volume and lower urinary tract symptom, and often are accompanied with erectile dysfunction, abnormal ejaculation, low libido and other side effects such as the feminization of male breast, breast pain etc. Thus, the most widely used drug in clinical is $\alpha_1$-adrenergic receptor antagonist.

Adrenergic receptors (ARs) are divided into α-receptors and β-receptors, and α-adrenergic receptors (α-ARs) are divided into two types of receptors, i.e., $\alpha_1$ and $\alpha_2$. Now three kinds of $\alpha_1$-receptor subtypes ($\alpha_{1A}$, $\alpha_{1B}$ and $\alpha_{1D}$) have been identified. Research shows that $\alpha_1$ receptors mainly present in prostate matrix components and glandular epithelium, in which $\alpha_{1A}$-AR accounts for about 70% of total $\alpha_1$-ARs in human prostate and urinary system. In reproductive and urinary system, $\alpha_{1A}$-receptors are mainly distributed in the prostate, urethra and bladder trigone, and vas deferens; $\alpha_{1B}$-receptors are mainly distributed in blood vessels; and $\alpha_{1D}$-receptors are mainly distributed in detrusor of bladder and ureter smooth muscle.

In BPH pathological cases, $\alpha_1$-ARs density is significantly increased. Additionally, distribution of $\alpha_1$-ARs subtypes is different when age changes. The correlation between age and distribution is significant for understanding and treatment of benign prostatic hyperplasia and lower urinary tract symptoms, and for development of $\alpha_1$-adrenergic receptor antagonists. $\alpha_{1A}$-adrenergic receptor is considered to be an ideal target for treatment of benign prostatic hyperplasia, and blocking it has been proved to effectively reduce frequency of prostate smooth muscle contraction and improve bladder evacuation simultaneously. Blocking $\alpha_{1B}$-adrenergic receptor leads to vascular smooth muscle relaxation, arteriovenous expansion, peripheral resistance decrease and other symptoms, and may cause side effects such as dizziness and hypotension in some patients. Activating $\alpha_{1D}$-adrenergic receptor can lead to detrusor hyperactivity, and blocking it can reduce occurrence of evacuation symptoms as proven in animal experiments. Theoretically, $\alpha_{1A}$ and $\alpha_{1D}$-adrenergic receptor dual inhibitors are very effective drugs for controlling benign prostatic hyperplasia, because it has two functions, i.e., reducing frequency of prostate smooth muscle contraction and inhibiting detrusor dysfunction, and, additionally, it can avoid cardiovascular side effects caused by $\alpha_{1B}$-adrenergic receptor blockade.

Phenoxybenzamine as the first generation of α receptor repressor is developed and utilized for effectively curing symptoms of benign prostatic hyperplasia. Phenoxybenzamine is an irreversible and non-selective $\alpha_1/\alpha_2$ receptor repressor and belongs to β-haloalkane, and it blocks α receptor in prostate and results in laxity of prostate fibrous tissue. Phenoxybenzamine is used in clinical to treat urination difficulty caused by non-mechanical urethra obstruction caused by prostate. Phenoxybenzamine contains β-chloroethylamine structure which easily reacts with other enzymes in body, thereby inducing toxicity and side effects. As a non-selective α-receptor repressor, phenoxybenzamine blocks $\alpha_1$-receptors and presynaptic $\alpha_2$ receptors, and causes feedback to the nerve endings to release norepinephrine, thereby inducing reflex tachycardia, arrhythmia and other side effects.

In order to reduce these side effects, the second generation of $\alpha_1$-adrenergic receptor antagonists are developed with a high selectivity for $\alpha_1$-receptor (such as: prazosin, terazosin, doxazosin, alfuzosin). $\alpha_1$-adrenergic receptor can alleviate prostate and urethra smooth muscle shrinkage caused by the sympathetic, and kinetically reduce symptoms of urethral obstruction. These drugs can effectively relieve lower urinary tract symptoms and reduce side effects caused by vasodilation. Prazosin drugs all have quinazoline nucleus structure, and are commonly used to treat lower urinary tract symptoms (LUTS) caused by BPH in clinical. However, due to widespread of $\alpha_1$-adrenergic receptor and important physiological functions, using $\alpha_1$-adrenergic receptor antagonists often lead to orthostatic hypotension, dizziness, weakness and other side effects.

In recent years, approved drugs for treating benign prostatic hyperplasia are $\alpha_{1A}$ receptor selective antagonists tamsulosin and silodosin. Tamsulosin is considered as $\alpha_{1A}$-receptor selective antagonists, but it has poor selectivity to other $\alpha_1$-receptors, and due to an earlier time on the market, it has a large market share. But it still has some side effects, such as side effects on immunity system and ocular region. Additionally, it may causes ejaculation disorders, lower blood pressure, headaches and other side effects. The drug silodosin which entered into market recently has good receptor selectivity which is better than that of tamsulosin, and now its side effects in clinic are less than those of tamsulosin. Therefore, the drugs having good $\alpha_{1A}$-receptor selectivity undoubtedly has good market prospect for treating benign prostatic hyperplasia.

SUMMARY OF THE INVENTION

One object of the present invention is to provide a pharmaceutical use of hexahydrodibenzo[a,g]quinolizine compound.

Another object of the present invention is to provide a medicine with better $\alpha_{1A}$-receptor selectivity for treatment of benign prostatic hyperplasia.

In the first aspect of the invention, it provides a use of hexahydrodibenzo[a,g]quinolizine compound of formula (I), or a pharmaceutically acceptable salt, solvate, stereoisomer, tautomer thereof for preparing a medicine for treating and/or preventing benign prostatic hyperplasia,

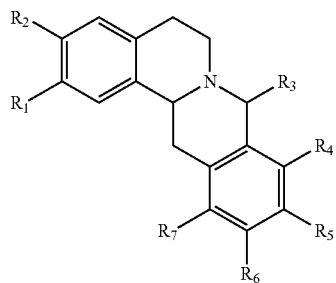

(I)

wherein, each of $R_1$, $R_2$, $R_4$, $R_5$, $R_6$ and $R_7$ is independently hydrogen, hydroxy, halogen, a substituted or unsubstituted C1-C6 alkoxy, a substituted or unsubstituted C1-C6 alkyl, a substituted or unsubstituted C2-C6 alkenyl, a substituted or unsubstituted C2-C6 alkynyl, a substituted or unsubstituted C3-C6 cycloalkyl, a substituted or unsubstituted benzyloxy, wherein a substituent for substitution is halogen, hydroxy, amino or sulfonyl;

$R_3$ is hydrogen, halogen, an unsubstituted or halogen-substituted C1-C6 alkyl, or an unsubstituted or halogen-substituted C1-C6 alkoxy;

$R_1$ and $R_2$ can together form a substituted or unsubstituted 5-7 membered heterocycle, wherein a substituent for substitution is halogen or a unsubstituted or halogen-substituted C1-C6 alkyl, and said heterocycle contains 1-3 heteroatoms selected from N, O, or S;

any two adjacent substituents of $R_4$, $R_5$, $R_6$ and $R_7$ can together form a substituted or unsubstituted 5-7 membered heterocycle, wherein a substituent for substitutions is halogen, an unsubstituted or halogen-substituted C1-C6 alkyl or a unsubstituted or halogen-substituted C1-C6 alkoxy, and said heterocycle contains 1-3 heteroatoms selected from N, O, or S;

the configuration of the chiral carbon atom in compound of general formula (I) is either R or S.

In one embodiment, each of $R_1$, $R_2$, $R_4$, $R_5$, $R_6$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, a substituted or unsubstituted benzyloxy, wherein a substituent for substitution is halogen, hydroxy, amino or sulfonyl;

$R_3$ is hydrogen, halogen, an unsubstituted or halogen-substituted C1-C4 alkyl, or an unsubstituted or halogen-substituted C1-C4 alkoxy;

$R_1$ and $R_2$ can together form a substituted or unsubstituted 5-7 membered heterocycle, wherein a substituent for substitution is halogen or an unsubstituted or halogen-substituted C1-C4 alkyl, and said heterocycle contains 1-3 heteroatoms selected from N, O, or S;

any two adjacent substituents of $R_4$, $R_5$, $R_6$ and $R_7$ can together form a substituted or unsubstituted 5-7 membered heterocycle, wherein a substituent for substitutions is halogen, a unsubstituted or halogen-substituted C1-C4 alkyl or a unsubstituted or halogen-substituted C1-C4 alkoxy, and said heterocycle contains 1-3 heteroatoms selected from N, O, or S;

the configuration of the chiral carbon atom in compound of general formula (I) is either R or S.

In one embodiment, each of $R_1$, $R_2$, $R_4$, $R_5$, $R_6$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution can be halogen, hydroxy, or amino;

$R_3$ is hydrogen, halogen, and an unsubstituted or halogen-substituted C1-C4 alkyl;

$R_1$ and $R_2$ can together form a substituted or unsubstituted 5 or 6 membered heterocycle, wherein a substituent for substitution is halogen or an unsubstituted or halogen-substituted C1-C4 alkyl, and said heterocycle contains 1-3 heteroatoms selected from N, O, or S;

any two adjacent substituents of $R_4$, $R_5$, $R_6$ and $R_7$ can together form a substituted or unsubstituted 5 or 6 membered heterocycle, wherein a substituent for substitutions is halogen, a unsubstituted or halogen-substituted C1-C4 alkyl or a unsubstituted or halogen-substituted C1-C4 alkoxy, and said heterocycle contains 1-3 heteroatoms selected from N, O, or S;

the configuration of the chiral carbon atom in compound of general formula (I) is either R or S.

In one embodiment, each of $R_1$, $R_2$, $R_4$, $R_5$, $R_6$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen, or hydroxy;

$R_3$ is hydrogen, halogen, or an unsubstituted or halogen-substituted C1-C4 alkyl;

$R_1$ and $R_2$ can together form a 5 or 6 membered heterocycle which contains 1 to 2 heteroatoms selected from N, O, or S;

$R_5$ and $R_6$ can together form a 5 or 6 membered heterocycle which contains 1 to 2 heteroatoms selected from N, O, or S;

the configuration of the chiral carbon atom in compound of general formula (I) is either R or S.

In one embodiment, the hexahydrodibenzo[a,g]quinolizine compounds of general formula (I) are selected from the following compounds:

| NO. | Structure |
|---|---|
| DC037001 | 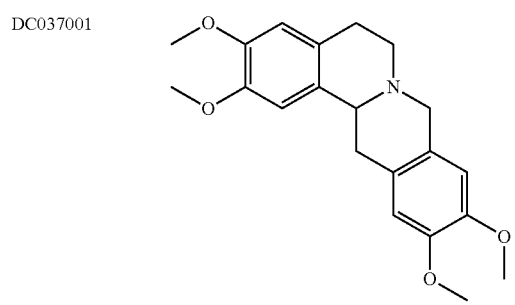 |
| DC037002 | 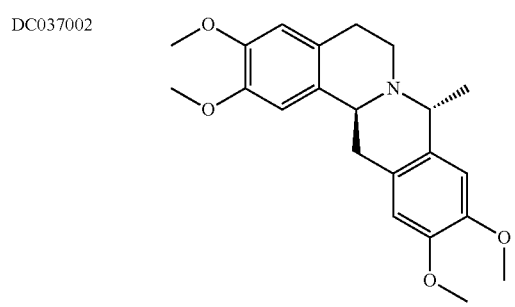 |
| DC037003 | 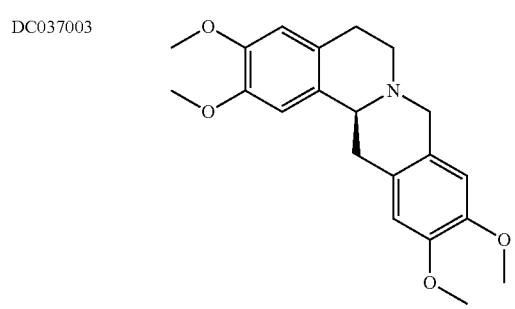 |
| DC037004 | 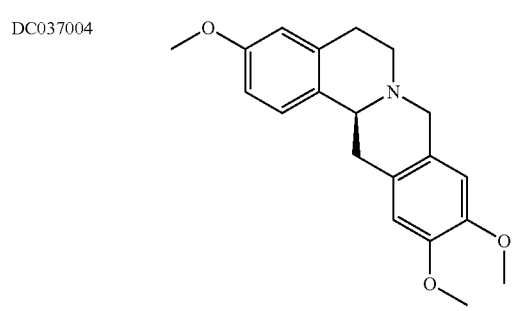 |
| DC037005 | 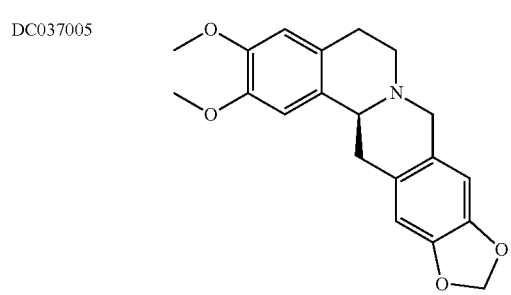 |
-continued
| NO. | Structure |
|---|---|
| DC037006 | 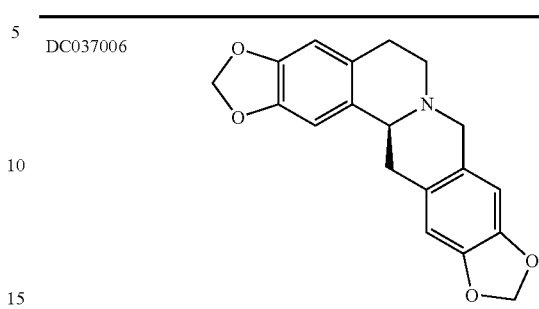 |
| DC037007 | 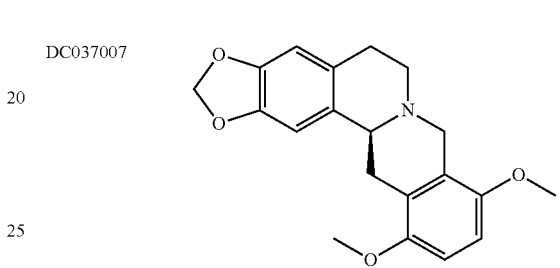 |
| DC037008 | 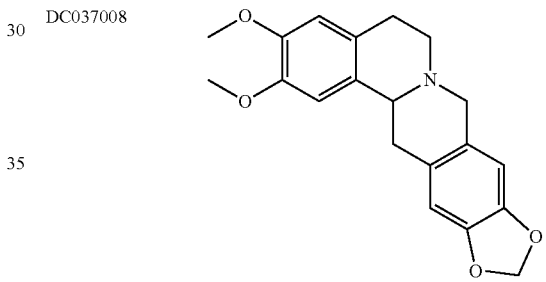 |
| DC037009 | 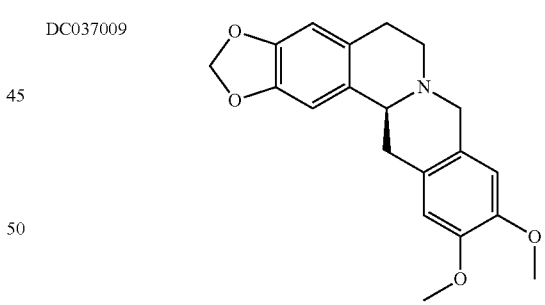 |
| DC037010 | 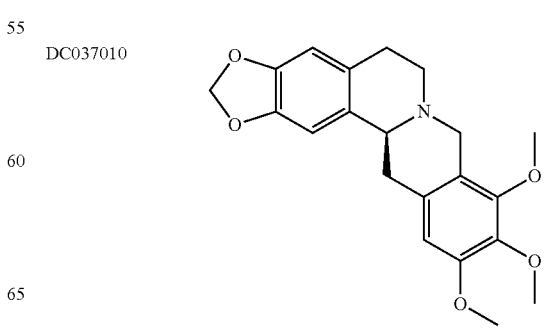 |

| NO. | Structure |
|---|---|
| DC037011 | 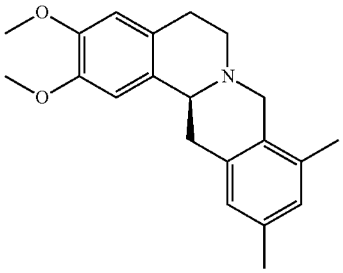 |
| DC037012 | 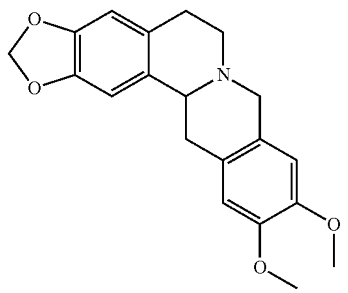 [SMILES: COc1cc2c(cc1OC)CN1CCc3cc4c(cc3C1C2)OCO4] |
| DC037013 | 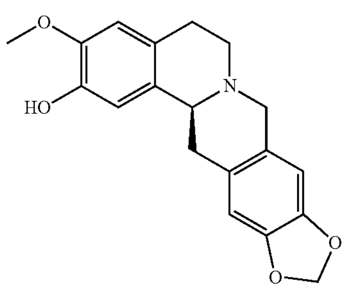 [SMILES: COc1cc2c(cc1O)[C@@H]1Cc3cc4c(cc3CN1CC2)OCO4] |
| DC037014 | 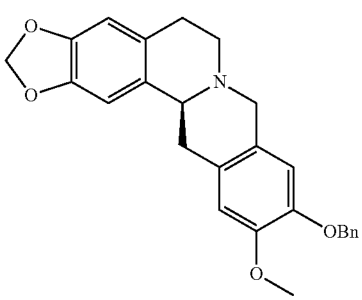 [SMILES: COc1cc2c(cc1OCc1ccccc1)CN1CCc3cc4c(cc3[C@@H]1C2)OCO4] |
| DC037015 | 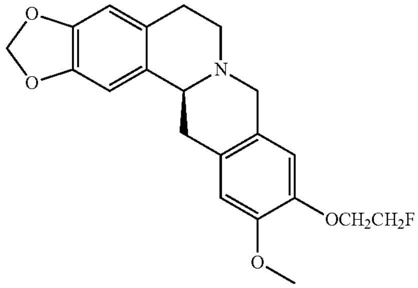 |

| NO. | Structure |
|---|---|
| DC037016 | 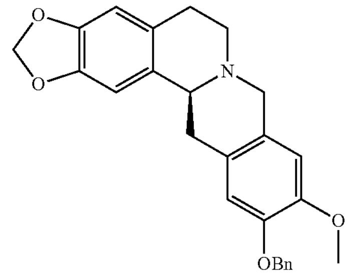 |
| DC037017 | 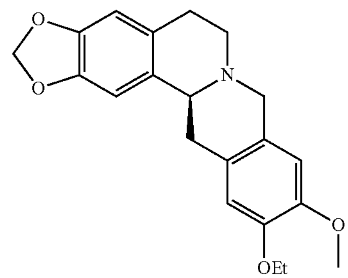 |
| DC037018 | 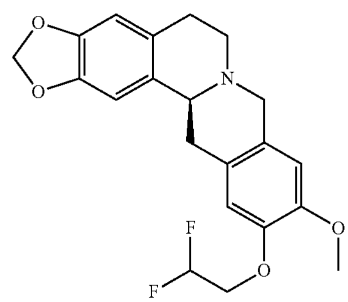 [SMILES: COc1cc2c(cc1OCC(F)F)C[C@H]1c3cc4c(cc3CCN1C2)OCO4] |
| DC037019 | 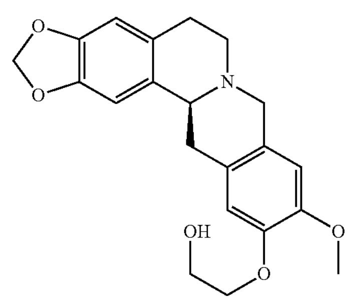 |
| DC037020 | 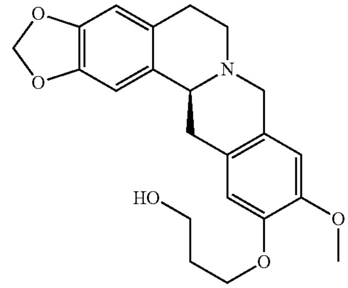 [SMILES: COc1cc2c(cc1OCCCO)C[C@H]1c3cc4c(cc3CCN1C2)OCO4] |

-continued

| NO. | Structure |
|---|---|
| DC037021 | (structure with methylenedioxy, hexahydrodibenzo[a,g]quinolizine core, OCH₃, and OCH₂CF₃ substituents) |
| DC037022 | (structure with methylenedioxy, hexahydrodibenzo[a,g]quinolizine core, OCH₃, and OCH₂CH₂CH₃ substituents) |
| DC037023 | (structure with methylenedioxy, hexahydrodibenzo[a,g]quinolizine core, OCH₃, and OCH₂CH₂CF₃ substituents) | wherein, the configuration of the unmarked chiral carbon atom is either R or S.

In one embodiment, the medicine is used for selectively binding to $\alpha_{1A}$-adrenergic receptors.

In one embodiment, $IC_{50}(\alpha_{1B}/\alpha_{1A})$ is ≥2, preferably ≥5, more preferably ≥10, wherein $IC_{50}(\alpha_{1A}/\alpha_{1A})$ is a ratio of $IC_{50}$ of said medicine binding to $\alpha_{1B}$-adrenergic receptors and $IC_{50}$ of said medicine binding to $\alpha_{1A}$-adrenergic receptors.

In one embodiment, $IC_{50}(\alpha_{1B}/\alpha_{1A})$ is 2-3000, wherein $IC_{50}(\alpha_{1B}/\alpha_{1A})$ is a ratio of $IC_{50}$ of said medicine binding to $\alpha_{1B}$-adrenergic receptors and $IC_{50}$ value of said medicine binding to $\alpha_{1A}$-adrenergic receptors.

In one embodiment, $IC_{50}$ of said medicine binding to $\alpha_{1B}$-adrenergic receptors is ≥150 nM, preferably ≥500 nM, and more preferably ≥1000 nM.

In one embodiment, said medicine is used to selectively inhibit contraction of urinary system smooth muscle.

In one embodiment, said urinary system smooth muscle is selected from urethra smooth muscle, and prostate smooth muscle.

In the second aspect of the invention, it provides an in vitro non-therapeutic method for inhibiting the $\alpha_{1A}$-adrenergic receptor, comprising a step of administering an inhibitively effective amount of a hexahydrodibenzo[a,g]quinolizine compound of general formula (I), or a pharmaceutically acceptable salt, solvate, stereoisomer, tautomer thereof to an object in need thereof.

In one embodiment, the inhibition is selective inhibition of $\alpha_{1A}$-adrenergic receptor.

In one embodiment, the object to be inhibited is a cell or animal in vitro tissue expressing $\alpha_{1A}$-adrenergic receptor.

In one embodiment, the object to be inhibited is a cell or animal in vitro tissue expressing $\alpha_{1A}$-adrenergic receptor and $\alpha_{1B}$-adrenergic receptor, and preferably, the object also expresses $\alpha_{1D}$-adrenergic receptor.

In one embodiment, the object to be inhibited is urethra smooth muscle, or prostate smooth muscle.

In the third aspect of the invention, it provides a method for preparing a pharmaceutical composition, comprising mixing a compound of general formula (I), or a pharmaceutically acceptable salt, solvate, stereoisomer, or tautomer thereof with a pharmaceutically acceptable carrier to form a pharmaceutical composition.

In one embodiment, the pharmaceutically acceptable carrier is selected from oral preparation carriers or injection carriers.

In the forth aspect of the invention, it provides a use of a compound of formula (I) compound in the first aspect of the invention for preparing a inhibitor selectively binding to $\alpha_{1A}$-adrenergic receptor.

In the fifth aspect of the invention, it provides a use of a compound of formula (I) in the first aspect of the invention, wherein the compound is used as inhibitor for treating prostate; and/or the compound is used for antagonizing norepinephrine-induced contraction of urethra smooth muscle and/or prostatic smooth muscle.

In the sixth aspect of the invention, it provides an $\alpha_{1A}$-adrenergic receptor selective inhibitor, which comprises an inhibitively effective amount of the compound of formula (I), or a pharmaceutically acceptable salt, solvate, stereoisomer, tautomer thereof.

In the seventh aspect of the invention, it provides a method for treating and/or preventing benign prostatic hyperplasia diseases, comprising a step of administering a therapeutically effective amount of the compound of formula (I), or a pharmaceutically acceptable salt, solvate, stereoisomer, tautomer thereof to a subject in need thereof.

In the eighth aspect of the invention, it provides a pharmaceutical composition for treating or inhibiting benign prostatic hyperplasia diseases, comprising (a) a pharmaceutically acceptable carrier, and (b) the compound of formula (I), or a pharmaceutically acceptable salt, solvate, stereoisomer, tautomer thereof.

In one embodiment, the formulation of the pharmaceutical composition is oral formulation or injection formulation.

It should be understood that in the present invention, the technical features specifically described above and hereinafter (such as the Examples) can be combined with each other, thereby constituting a new or preferred technical solution, which needs not be specified one by one.

DETAILED DESCRIPTION OF INVENTION

Figure 1:
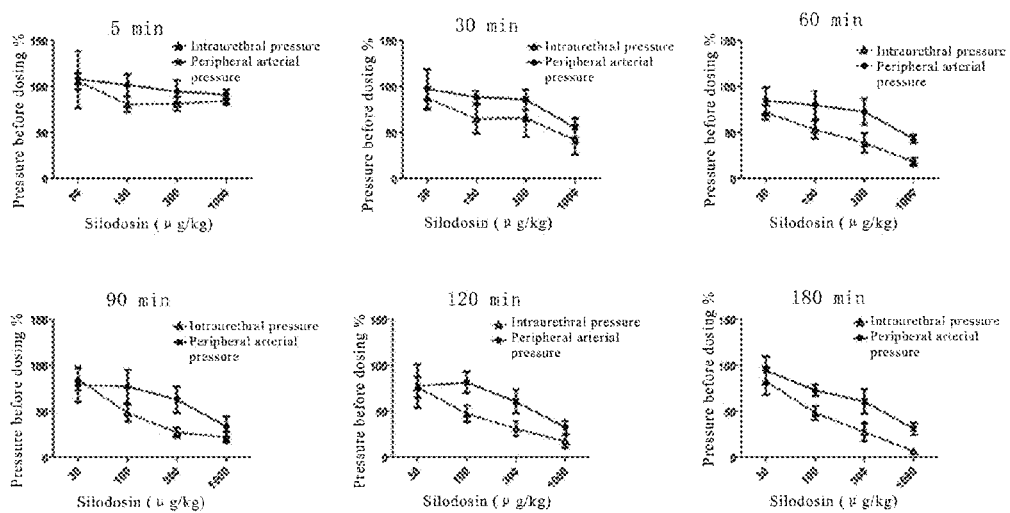
FIG. 1 is an experimental curve in Example 4 of invention showing effects of positive drug silodosin on rat urethral pressure (IUP), and peripheral arterial pressure (MBP).

Through intensive and long-term research, the inventors have unexpectedly discovered that, hexahydrodibenzo[a,g]quinolizine compounds can selectively binding to $\alpha_{1A}$-adrenergic receptor and not binding to $\alpha_{1B}$-adrenergic receptor, and therefore can be used for preparing medicines for controlling benign prostatic hyperplasia with reduced cardiovascular side effects. Based on this discovery, the inventors have completed the present invention.

Definition

The term "C1-C6 alkoxy" refers to a straight or branched alkoxy having 1-6 carbon atoms, such as methoxy, ethoxy, propoxy, isopropoxy, butoxy, isobutoxy, sec-butoxy, tert-butoxy, and the like.

The term "C1-C6 alkyl" refers to a straight or branched alkyl having 1-6 carbon atoms, such as methyl, ethyl, propyl, isopropyl, butyl, isobutyl, sec-butyl, tert-butyl, and the like.

The term "C3-C6 cycloalkyl" refers to a cycloalkyl group having 3-6 carbon atoms, such as cyclopropyl, cyclobutyl, cyclopentyl, cycloheptyl, and the like.

The term "C2-C6 alkenyl" refers to an alkenyl group having 1-6 carbon atoms, such as ethenyl, propenyl, isopropenyl, butenyl, isobutenyl, sec-butenyl, tert-butenyl, and the like.

The term "C2-C6 alkynyl" refers to an alkynyl group having 1-6 carbon atoms, such as ethynyl, propynyl, iso-alkynyl, butynyl, iso-alkynyl, sec-butynyl, tert-butynyl group, and the like.

The term "sulfonyl" refers to a group having "C1-C6 alkyl-SO$_2$—" or "aryl-SO$_2$—" structure, such as methylsulfonyl, ethylsulfonyl, propylsulfonyl, isopropylsulfonyl, butylsulfonyl, iso-butylsulfonyl, sec-butylsulfonyl, tert-butylsulfonyl, benzenesulfonyl, tosyl and the like.

The term "5-7 membered heterocycle" refers to a cyclic structure having one or more and preferably 1-3 heteroatoms, and said heterocycle is saturated or unsaturated. In particular, "R$_1$ and R$_2$ can together form a heterocycle" means that R$_1$, R$_2$ and form a heterocyclic ring together with a carbon chain to which they are attached.

The term "halogen" refers to F, Cl, Br and I.

As used herein, the term "Rx and Ry (x and y are selected from 1, 2, 4, 5, 6, 7) can together form a substituted or unsubstituted m-membered heterocycle (m=5, 6 or 7)" means that Rx, Ry and 1-3 adjacent carbon atoms together form a substituted or unsubstituted m-membered heterocycle (m=5, 6 or 7).

As used herein, the term "the configuration of the chiral carbon atom is either R or S" means that the chiral carbon atom in the structural formula may be R configuration, S configuration, or a mixture thereof, and preferably is a single R configuration or S configuration.

Pharmaceutically Acceptable Salt, Solvate, Stereoisomer, Tautomer

As used herein, the term "pharmaceutically acceptable salt" refers to salts formed by a compound of the present invention with a pharmaceutically acceptable inorganic and organic acid. The preferred inorganic acid includes (but is not limited to): hydrochloric acid, hydrogen bromic acid, phosphoric acid, nitric acid, sulfuric acid; and preferred organic acid includes (but is not limited to): formic acid, acetic acid, propionic acid, succinic acid, naphthalene dicarboxylic acid (1,5), asiatic acid, oxalic acid, tartaric acid, lactic acid, salicylic acid, benzoic acid, pentanoic acid, diethyl acetic acid, malonic acid, succinic acid, fumaric acid, pimelic acid, adipic acid, maleic acid, malic acid, sulfamic acid, phenylpropionic acid, gluconic acid, ascorbic acid, nicotinic acid, isonicotinic acid, methanesulfonic acid, p-toluenesulfonic acid, citric acid, and amino acid.

As used herein, the term "pharmaceutically acceptable solvate" refers to a solvate formed by a compound of the present invention with a pharmaceutically acceptable solvent, wherein the pharmaceutically acceptable solvent includes (but is not limited to): water, ethanol, methanol, isopropanol, tetrahydrofuran, and methylene chloride.

As used herein, the term "pharmaceutically acceptable stereoisomer" refers to a compound of the present invention in which the chiral carbon atom is R configuration, or S configuration, or a combination thereof.

Pharmaceutical Composition

The present invention also provides a pharmaceutical composition, which has significant efficacy which comprises a therapeutically effective amount of a compound of formula I, or a pharmaceutically acceptable salt thereof, and one or more pharmaceutically acceptable carriers.

A mixture formed by compound itself or a pharmaceutically acceptable salt thereof with a pharmaceutically acceptable excipient or diluent, can be orally administered in the form of tablets, capsules, granules, powders or syrups, or non-orally administered in the form of injection. The pharmaceutical composition preferably contains 0.01-99 wt % of the compound of formula I or a pharmaceutically acceptable salt thereof as an active ingredient, and more preferably contains 0.1-90 wt % of the active ingredient.

The above formulations may be prepared by conventional methods of pharmacy. Examples of available pharmaceutically acceptable adjuvants include excipients (e.g. sugar derivatives such as lactose, sucrose, glucose, mannitol and sorbitol; starch derivatives such as corn starch, potato starch, dextrin and carboxymethyl starch; cellulose derivatives such as crystalline cellulose, hydroxypropyl cellulose, carboxymethyl cellulose, carboxymethyl cellulose calcium, carboxymethyl cellulose sodium; gum arabic; dextran; silicate derivative such as metasilicate magnesium aluminum; phosphate derivatives such as calcium phosphate; carbonate derivatives such as calcium carbonate; sulfate derivatives such as calcium sulfate), binders (e.g., gelatin, polyvinyl pyrrolidone, and polyethylene glycols), disintegrants (e.g., cellulose derivatives such as sodium carboxymethyl cellulose, polyvinylpyrrolidone), lubricants (e.g., talc, calcium stearate, magnesium stearate, spermaceti, boric acid, sodium benzoate, leucine), stabilizers (methyl paraben, propyl paraben, etc.), flavoring agents (e.g., common sweeteners, sour agents and perfumes and the like), diluents and injection solvent (such as water, ethanol and glycerol, etc.).

The compound of the invention, pharmaceutically acceptable salt or prodrug thereof, or the pharmaceutical composition thereof can be administrated in different dosage which varies with age, gender, race, and diseases.

New pharmaceutical use of hexahydrodibenzo[a,g]quinolizine compound

The present invention provide a use of hexahydrodibenzo[a,g]quinolizine compound of formula (I), or a pharmaceutically acceptable salt, solvate, stereoisomer, tautomer thereof for preparing a medicine for treating and/or preventing benign prostatic hyperplasia,

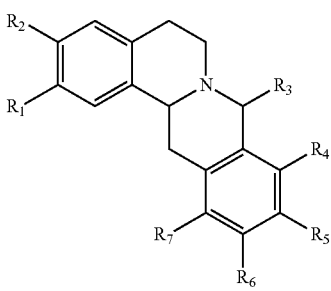
(I)

wherein, each of $R_1$, $R_2$, $R_4$, $R_5$, $R_6$ and $R_7$ is independently hydrogen, hydroxy, halogen, a substituted or unsubstituted C1-C6 alkoxy, a substituted or unsubstituted C1-C6 alkyl, a substituted or unsubstituted C2-C6 alkenyl, a substituted or unsubstituted C2-C6 alkynyl, a substituted or unsubstituted C3-C6 cycloalkyl, a substituted or unsubstituted benzyloxy, wherein a substituent for substitution is halogen, hydroxy, amino or sulfonyl;

$R_3$ is hydrogen, halogen, an unsubstituted or halogen-substituted C1-C6 alkyl, or an unsubstituted or halogen-substituted C1-C6 alkoxy;

$R_1$ and $R_2$ can together form a substituted or unsubstituted 5-7 membered heterocycle, wherein a substituent for substitution is halogen or an unsubstituted or halogen-substituted C1-C6 alkyl, and said heterocycle contains 1-3 heteroatoms selected from N, O, or S;

any two adjacent substituents of $R_4$, $R_5$, $R_6$ and $R_7$ can together form a substituted or unsubstituted 5-7 membered heterocycle, wherein a substituent for substitutions is halogen, a unsubstituted or halogen-substituted C1-C6 alkyl or an unsubstituted or halogen-substituted C1-C6 alkoxy, and said heterocycle contains 1-3 heteroatoms selected from N, O, or S;

the configuration of the chiral carbon atom in compound of general formula (I) is either R or S.

Preferably, in compound of formula (I), each of $R_1$, $R_2$, $R_4$, $R_5$, $R_6$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, a substituted or unsubstituted benzyloxy, wherein a substituent for substitution is halogen, hydroxy, amino or sulfonyl;

$R_3$ is hydrogen, halogen, an unsubstituted or halogen-substituted C1-C4 alkyl, or an unsubstituted or halogen-substituted C1-C4 alkoxy;

$R_1$ and $R_2$ can together form a substituted or unsubstituted 5-7 membered heterocycle, wherein a substituent for substitution is halogen or unsubstituted or halogen-substituted C1-C4 alkyl, and said heterocycle contains 1-3 heteroatoms selected from N, O, or S;

any two adjacent substituents of $R_4$, $R_5$, $R_6$ and $R_7$ can together form a substituted or unsubstituted 5-7 membered heterocycle, wherein a substituent for substitutions is halogen, a unsubstituted or halogen-substituted C1-C4 alkyl or a unsubstituted or halogen-substituted C1-C4 alkoxy, and said heterocycle contains 1-3 heteroatoms selected from N, O, or S;

the configuration of the chiral carbon atom in compound of general formula (I) is either R or S.

More preferably, in formula (I) compound, each of $R_1$, $R_2$, $R_4$, $R_5$, $R_6$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen, hydroxy, or amino;

$R_3$ is hydrogen, halogen, an unsubstituted or halogen-substituted C1-C4 alkyl;

$R_1$ and $R_2$ can together form a substituted or unsubstituted 5 or 6 membered heterocycle, wherein a substituent for substitution is halogen or an unsubstituted or halogen-substituted C1-C4 alkyl, and said heterocycle contains 1-3 heteroatoms selected from N, O, or S;

any two adjacent substituents of $R_4$, $R_5$, $R_6$ and $R_7$ can together form a substituted or unsubstituted 5 or 6 membered heterocycle, wherein a substituent for substitutions is halogen, a unsubstituted or halogen-substituted C1-C4 alkyl or a unsubstituted or halogen-substituted C1-C4 alkoxy, and said heterocycle contains 1-3 heteroatoms selected from N, O, or S;

the configuration of the chiral carbon atom in compound of general formula (I) is either R or S.

Further preferably, in compound of formula (I), each of $R_1$, $R_2$, $R_4$, $R_5$, $R_6$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen, or hydroxy;

$R_3$ is hydrogen, halogen, an unsubstituted or halogen-substituted C1-C4 alkyl;

$R_1$ and $R_2$ can together form a 5 or 6 membered heterocycle which contains 1 to 2 heteroatoms selected from N, O, or S;

$R_5$ and $R_6$ can together form a 5 or 6 membered heterocycle which contains 1 to 2 heteroatoms selected from N, O, or S; and the configuration of the chiral carbon atom in compound of general formula (I) is either R or S.

The halogen is F, Cl, Br or I.

The most preferred hexahydrodibenzo[a,g]quinolizine compounds of the invention including a pharmaceutically acceptable salt, solvate, stereoisomer, tautomer thereof are selected from the following compounds:

| NO. | Structure |
|---|---|
| DC037001 | 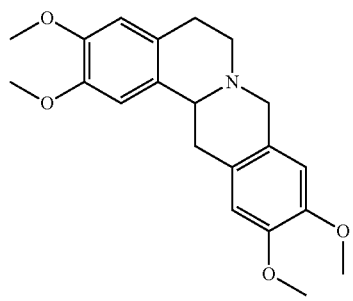 |
| DC037002 | 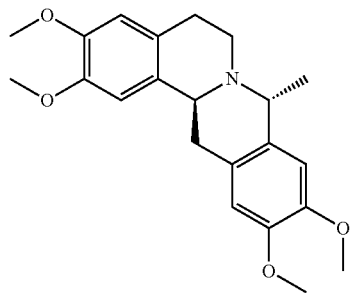 |

-continued

| NO. | Structure |
|---|---|
| DC037003 | 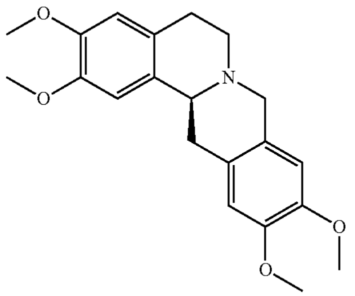 |
| DC037004 | 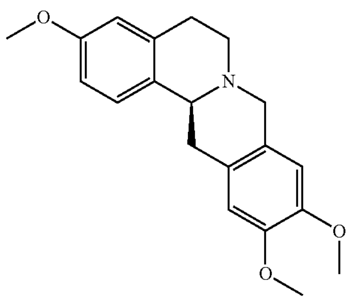 |
| DC037005 | 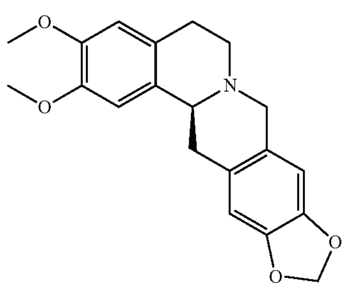 [SMILES: COc1cc2c(cc1OC)[C@@H]1Cc3cc4c(cc3CN1CC2)OCO4] |
| DC037006 | 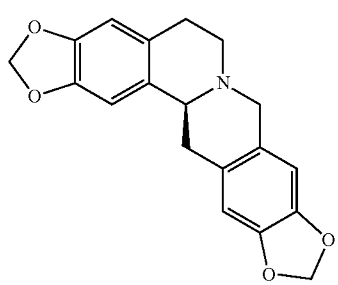 [SMILES: c1c2c(cc3c1OCO3)CN1CCc3cc4c(cc3[C@@H]1C2)OCO4] |
| DC037007 | 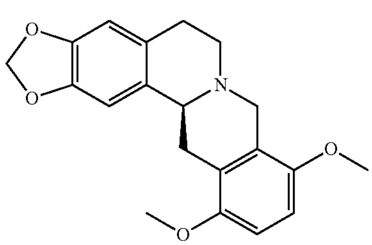 [SMILES: COc1ccc(OC)c2c1C[C@H]1c3cc4c(cc3CCN1C2)OCO4] |

-continued

| NO. | Structure |
|---|---|
| DC037008 | |
| DC037009 | |
| DC037010 | |
| DC037011 | |
| DC037012 | |

| NO. | Structure |
|---|---|
| DC037013 | 2-methoxy, 3-hydroxy berberine-type structure with methylenedioxy |
| DC037014 | methylenedioxy berberine-type with OBn, OMe substituents |
| DC037015 | methylenedioxy berberine-type with OCH₂CH₂F and OMe substituents |
| DC037016 | methylenedioxy berberine-type with OMe and OBn substituents |
| DC037017 | methylenedioxy berberine-type with OMe and OEt substituents |
| DC037018 | methylenedioxy berberine-type with OMe and OCH₂CHF₂ substituents |
| DC037019 | methylenedioxy berberine-type with OMe and OCH₂CH₂OH substituents |
| DC037020 | methylenedioxy berberine-type with OMe and OCH₂CH₂CH₂OH substituents |
| DC037021 | methylenedioxy berberine-type with OMe and OCH₂CF₃ substituents |
| DC037022 | methylenedioxy berberine-type with OMe and O-n-propyl substituents |

| NO. | Structure |
|---|---|
| DC037023 | (structure: methylenedioxy-dibenzo[a,g]quinolizine with OMe and OCH2CF3 substituents) |

The most preferred compound of present invention is S-(-)-2,3-methylenedioxy-10,11-dimethoxy-5,8,13,13a-tetrahydro-6H-dibenzo[a,g]quinolizine (DC037009), including a pharmaceutically acceptable salt, solvate, stereoisomer, tautomer thereof.

Pharmaceutical composition containing hexahydrodibenzo[a,g]quinolizine compounds Another object of the present invention is to provide a pharmaceutical composition comprising the compound of formula (I), or a pharmaceutically acceptable salt, solvate, stereoisomer, tautomer, prodrug thereof and a pharmaceutically acceptable carrier.

The present invention relates to a medicine for treating and/or preventing benign prostatic hyperplasia which is prepared using hexahydrodibenzo[a,g]quinolizine compounds as shown in formula (I) or a pharmaceutically acceptable salt, solvate, stereoisomer, tautomer, prodrug or the mixture thereof as an active ingredient.

The medicine can be introduced into body such as muscle, intradermal, subcutaneous, intravenous, mucosal tissue by injection, spray, nasal inhalation, eye drop, penetration, absorption, physical or chemical-mediated method; or the medicine is mixed with or wrapped by other substances before being introduced into body.

When necessary, one or more pharmaceutically acceptable carriers can be added into the above-mentioned medicine. The carriers include diluents, excipients, fillers, binders, wetting agents, disintegrators, absorption promoters, surfactant, adsorption carrier, lubricant and the like which are conventional in the pharmaceutical field.

The hexahydrodibenzo[a,g]quinolizine compounds as shown in formula (I) or a pharmaceutically acceptable salt, solvate, stereoisomer, tautomer, or prodrug thereof as an active ingredient can be used alone or in combination with other medicines, or is mixed with auxiliary materials and formulated into various preparations, including but not limited to tablets, powders, pills, injections, capsules, films, suppositories, paste, granules and so on. The above various preparations can be prepared according to conventional methods in the field of pharmacy.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning: A Laboratory Manual (New York: Cold Spring Harbor Laboratory Press, 1989)), or according to the manufacture's instructions. Unless indicated otherwise, parts and percentage are calculated by weight. The reagents and biological materials are commercially available if there is no specified description.

Example 1

Research of Activity on Cell and Selectivity of Drugs

HEK293 cells stably expressing α1A-AR/Gα16, α1B-AR/Gα16, α1D-AR/Gα16 were seeded in a 96-well plate, and cultured for 24 hours. Then the medium was removed and 40 μL Hank's balanced salt solution (HBSS: containing 5.4 mM KCl, 0.3 mM $Na_2HPO_4$, 0.4 mM $KH_2PO_4$, 4.2 mM $NaHCO_3$, 1.3 mM $CaCl_2$, 0.5 mM $MgCl_2$, 0.6 mM $MgSO_4$, 137 mM NaCl, 5.6 mM D-glucose, and 250 μM sulfinpyrazone, pH 7.4) containing 2 μM Fluo-4 AM was added into each well, and incubated at 37° C. for 45 min. Dye was removed and 50 μL of HBSS containing either test compound or 1% DMSO (negative control) was added. After incubation at room temperature for 10 min, Flex Station 3 microplate reader was used to read the value. At specified time points, 25 μL of agonist (phenylephrine, final concentration 30 nM) was dispensed into the well automatically using the reader and fluorescence intensity change of dye caused by intracellular calcium concentration change was detected at an excitation wavelength of 485 nm and an emission wavelength of 525 nm.

After incubation with different drugs, the reaction rate of cells to 1-AR agonist phenylephrine was calculated as follows:

Reaction rate %=(D−B)/(S−B)*100%;

wherein D is calcium mobilization signal peak provoked by phenylephrine after incubation with the test drug, B is calcium mobilization signal peak provoked by phenylephrine after incubation with 10 μM positive control drug tamsulosin, S is calcium mobilization signal peak provoked by phenylephrine after incubation with negative control of 1% DMSO.

The reaction rate of the same drug at different doses was tested using GraphPad Prism software by non-linear regression analysis, and the dose-response curve was obtained and IC50 values was measured. Data were obtained from three separate experiments, and each experiment included three duplicate wells.

TABLE 1

Data of activity on cell and selectivity of some compounds

| No. | $\alpha_{1A}$ (IC$_{50}$ nM) | $\alpha_{1B}$ (IC$_{50}$ nM) | $\alpha_{1D}$ (IC$_{50}$ nM) | $\alpha_{1B}/\alpha_{1A}$ |
|---|---|---|---|---|
| DC037001 | 122.5 | 173.9 | 8711 | 1.4 |
| DC037002 | 502.3 | 17178 | 2516 | 34.2 |
| DC037003 | 91.32 | 249369 | 2480 | 2731 |
| DC037004 | 93.87 | 189.4 | 422.5 | 2.0 |
| DC037005 | 159.8 | 1653 | 2953 | 10.3 |
| DC037007 | 968.7 | 12966 | 75.85 | 13.4 |
| DC037008 | 552.3 | 68790 | 2118 | 125 |
| DC037009 | 29.76 | 5207 | 260.3 | 175 |
| DC037010 | 237.7 | 1198 | 2557 | 5.0 |
| DC037011 | 531.6 | 34251 | 2645 | 64.4 |
| DC037012 | 257.1 | 7519 | 241.8 | 29.2 |
| DC037013 | 267.7 | 4305 | 263.2 | 16.1 |
| DC037014 | 303.3 | 35948 | 1340 | 118.5 |
| DC037016 | 34.84 | 4251 | 190.6 | 122 |
| Tamsulosin | 1.85 | 3.08 | 0.18 | 1.7 |

Cell experiments showed that although the activity of compounds including DC037009 on $\alpha_{1A}$-receptor was slightly weaker than that of positive drug tamsulosin, the selectivity of compounds on $\alpha_{1A}$-receptor was significantly better than those of tamsulosin, indicating these compounds were worthy of further study.

Example 2

Research of Binding Activity of the Drugs to Receptor

Tag-lite assay was used to study receptor binding activity. Tag-lite assay was a combination of SNAP-Tag and HTRF technology, and was used to analyze surface receptors on live cell. SNAPs were small tag fusion proteins which could irreversibly, specifically and covalently bind to substrates via benzylmethyl, and the substrates were benzylmethyl guanine and benzylmethyl cytosine. Substrates and various dyes formed derivatives, and through covalent reaction, the dye was labeled onto SANPs. Plasmid was constructed using pSNAP and $\alpha_1$-AR encoding gene. After transfection into cells, N-terminal fusion protein of SNAP and α1-AR was expressed. The substrate and HTRF fluorescent dye (donor compound Lumi4-Tb) formed a derivative which reacted with SANP-α1-AR fusion protein so that Tb was labeled onto α1-AR. After adding acceptor fluorescent dye-labeled ligand, the receptor and ligand binding experiment was performed.

HEK293 cells stably expressing SNAP-α1A-AR, SNAP-α1B-AR, SNAP-α1D-AR were seeded in 3 cm dishes, and cultured for 24 hours. 100 nM Tag-lite SNAP Lumi4Tb was added and incubated for 1 h in an incubator. Cells were detached and washed with a labeling buffer for 4 times, and then was added into a 384-well plate in a volume of 10 μL per well. 5 μL test compound and 5 μL red fluorescein-labeled known ligand with gradually increased concentration were added. After incubation at room temperature for 1 hour, fluorescence intensity changes caused by cell receptor and ligand changes were detected using 665 nm (acceptor) and 620 nm (donor) at same time.

After incubation with different drugs, the reaction rate of cells to 1-AR fluorescein-labeled known ligand was calculated as follows:

Reaction rate %=(D−B)/(S−B)*100% wherein D is signal peak provoked by fluorescein-labeled known ligand after incubation with test drug, B is signal peak provoked by 10 μM positive control drug tamsulosin, and S is signal peak provoked by negative control DMSO.

The reaction rate of the same drug at different doses was tested using GraphPad Prism software by non-linear regression analysis, and the dose-response curve was obtained and $K_i$ values was measured. Data were obtained from three separate experiments, and each experiment includes three duplicate wells.

TABLE 2

The receptor binding activity of some compounds

| No. | $\alpha_{1A}$ (IC$_{50}$ nM) | $\alpha_{1B}$ (IC$_{50}$ nM) | $\alpha_{1B}/\alpha_{1A}$ |
|---|---|---|---|
| DC037009 | 2.83 | 128.3 | 45.3 |
| DC037016 | 16.56 | 560.2 | 33.8 |
| DC037018 | 0.95 | 48.62 | 51.2 |
| Silodosin | 0.07 | 0.61 | 8.7 |
| Tamsulosin | 0.44 | 0.16 | 0.4 |

Cell experiments showed that although the activity of compounds including DC037009 on $\alpha_{1A}$-receptor was slightly weaker than those of positive drug tamsulosin and silodosin, the selectivity of compounds on $\alpha_{1B}$ was significantly better than those of positive control drugs, indicating such compounds were worthy of further study.

Example 3

Research of Activity of the Drugs to Animal Isolated Tissues

In Vitro Urethra Smooth Muscle Experiment:
Healthy male Wistar rats were hit head to cause faint. The abdominal cavity and the pubic symphysis was quickly cut so as to quickly remove the prostatic urethra, which was immediately placed into a dish filled with 4° C. Kerbs-Henseleit solution (K-H solution). The surrounding tissue were carefully separated, and muscle strips about 3-5 mm were obtained, and the lower end was fixed onto a 20 mL of thermostatic bath and the upper end was connected onto a pressure transducer. Nutrient liquid was K-H solution, and carbogen (95% oxygen and 5% carbon dioxide) was aerated, and the bath temperature was 37° C., and resting tension applied was 0.5 g. The nutrient liquid was replaced every 6-8 mins. Until baseline stabilized, norepinephrine was added with a final concentration of $3 \times 10^{-4}$ mol/L in bath tube. When the contraction curve reached the highest point, it was rinsed immediately to recover to baseline levels. When baseline was stabilized, test drug with different concentrations was added respectively, and incubated 3-5 mins. 60 μL $1 \times 10^{-1}$ M norepinephrine was added with a final concentration of $3 \times 10^{-4}$ mol/L in bath tube, and the contraction curve was recorded.

In Vitro Vascular Smooth Muscle Experiment:
Healthy male Wistar rats were hit head to cause faint. The abdominal cavity was quickly cut, and the thoracic aorta was taken out. The attached tissue was separated and cut into 2-3 mm vascular rings. The experiment was carried out in the same manner as in urethral smooth muscle experiment. The resting tension applied was 1 g, and when baseline was stabilized, norepinephrine was added with a final concentration of $10^{-7}$ mol/L in bath tube. When the contraction curve reached the highest point, rinse was performed immediately to recover to baseline levels. When baseline was stabilized, test drug with different concentrations was added respectively, and incubated 3-5 mins. 20 μL $1 \times 10^{-4}$ M norepinephrine was added with a final concentration of $10^{-7}$ mol/L in bath tube, and contraction curve was recorded.

TABLE 3

Data of experiments of compounds on isolated rat tissues

| No. | Urethra contraction (IC$_{50}$ nM) | Aorta contraction (IC$_{50}$ nM) | Urethra inhibition rate (%) | Aorta/ Urethra |
|---|---|---|---|---|
| DC037009 | 1.66 | 1417 | 80 | 873 |
| DC037016 | 5.12 | 10000 | 38 | 1953 |
| DC037018 | 146.8 | 2213 | 61 | 61 |
| Tamsulosin | 0.47 | 0.25 | 82 | 0.53 |
| Silodosin | 0.82 | 62.96 | 88 | 76.8 |

As for DC037009 compound, it showed an obvious antagonistic effect on norepinephrine-induced urethra smooth muscle contraction (IC50=1.66 nM), which is significantly stronger than the inhibition of norepinephrine-induced vascular smooth muscle contraction, and the receptor selectivity ratio reached 873 and the urethra suppression rate was comparable to that of the positive drugs. The selectivity of DC037009 was better than those of tamsulosin and silodosin, because it was 1671 folds of that of tamsulosin and 11 folds of that of Silodosin. It suggested that it was very important to reduce side effects of existing drugs.

Example 4

Pharmacological Research

Male SD rats (200-450 g) were anesthetized with an i.p. administration of urethane (1.25 g/kg). The urinary bladder, prostate, and urethra were exposed through an abdominal midline and symphysis pubica incision. A catheter was placed into the prostatic urethra through the bladder dome and secured at bladder neck (vesico-urethral junction) with a silk suture. The distal urethra under pubica was closed. The other side of the catheter was connected to a pressure transducer to measure the intraurethral pressure (IUP). After separating the duodenum and cutting open at about 2 cm from the stomach pylorus, intubating and performing purse-string suture, the test sample was supplied. Then, the median carotid incision was performed, carotid artery was separated, and the arterial blood pressure was measured by pressure transducer connected to artery cannula. Be careful not to hurt the nerves and blood vessels throughout the procedure. After surgery, a small amount (0.1~0.2 mL) of saline was injected to balance the intraurethral pressure at around 10 cm of water. Then an intravenous injection at a concentration of 30 μg/mL of hydrochloride (PHE) 1 mL/kg was performed before administration and 5 min, 30 min, 1 h, 1.5 h, 2 h, 3 h after administration to induce intraurethral pressure elevation. (If the effect was stable or weakened, then the experiment was ended.) The changes of intraurethral pressure and blood pressure induced by phenylephrine in rats were observed and recorded at different time points before and after administration.

Figure 2:
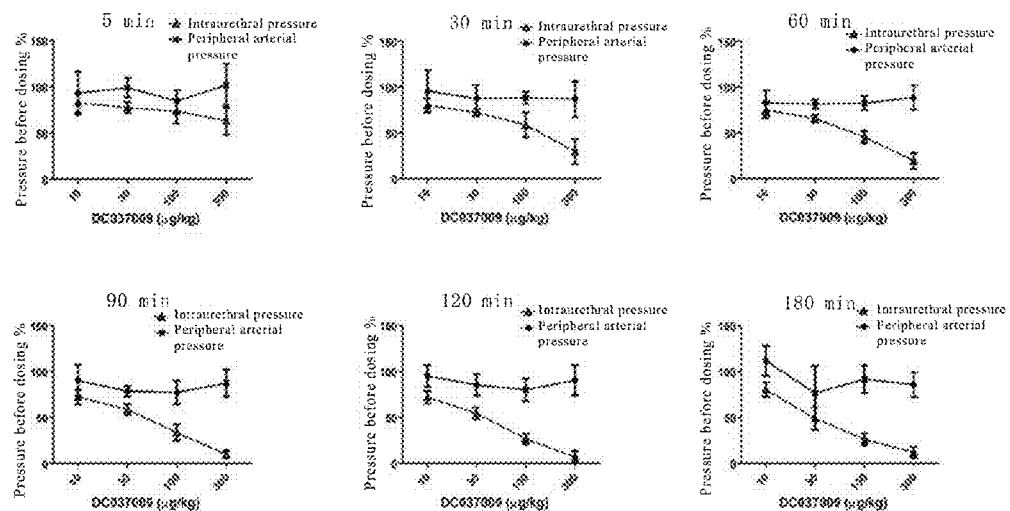
FIG. 2 is an experimental curve in Example 4 of invention showing effects of DC037009 on rat urethral pressure (IUP) and peripheral arterial pressure (MBP).

Experimental results showed that silodosin and DC037009 could dose-dependently inhibit the phenylephrine-induced intraurethral pressure (IUP) and peripheral arterial blood pressure (MBP) elevation. The inhibition of phenylephrine-induced intraurethral pressure elevation was as follows: DC037009>Silodosin. The inhibition of phenylephrine-induced blood pressure elevation was Silodosin>DC037009. The selectivity to urethra was DC037009>Silodosin. Additionally, the onset dose of DC037009 was significantly lower than that of positive drug silodosin (see FIG. 1 and FIG. 2).

Example 5

Pharmacodynamic Experiment

Establishing of BPH Rat model: 6-week-old male SD rats (n=49) (body weight about 200 g), in which 37 rats were BPH model group and daily injected testosterone propionate subcutaneously, and the other 12 rats were Sham group and injected olive oil, for 4 weeks. After 4 weeks, 49 rats received gavage in a dosage of 30 mL/kg of water, and urination for each rat was observed and recorded (recording each urine output and frequency of urination within two hours).

Figure 3:
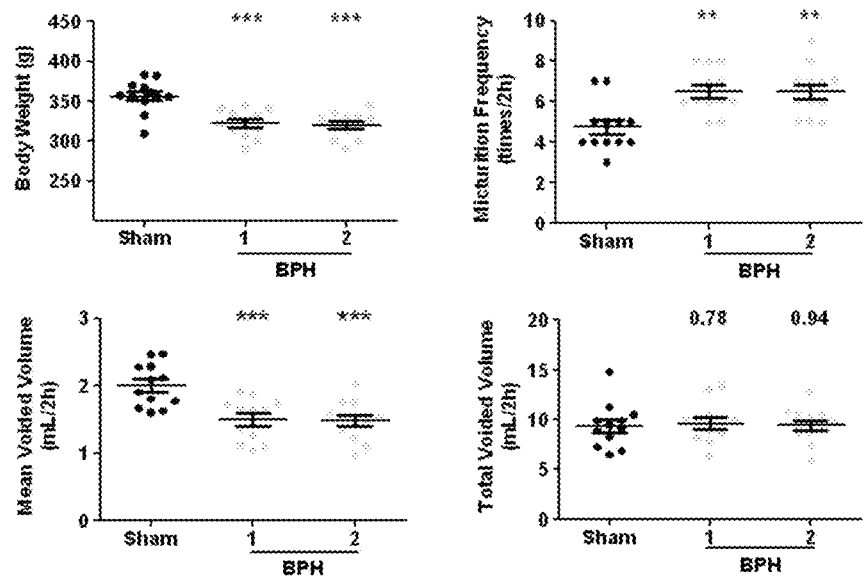
FIG. 3 shows micturition frequency, mean voided volume, total voided volume of rats in Sham group and BPH group in Example 5 of invention.

According to the above verification results, rats having abnormal urination were firstly excluded. Then, the normal BPH model rats were divided into 2 groups, 12 rats every group, and 12 rats of Sham group were singled out as control group. Grouping principles were as follows: there were significant differences of body weight, frequency of urination within two hours, single urine output and the total amount of urination between the two groups of BPH model and Sham group, and there were no significant differences between the two groups of BPH model. The results showed that two groups of BPH model rats is significantly different from Sham group in body weight, frequency of urination within two hours, and single urine output while there was no difference in frequency of urination and the total amount of urination (FIG. 3).

Efficacy verification experiment. The experiment had seven groups: Sham group, silodosin group (BPH-1,3-group dose) and DC037009 group (BPH-2,3-group dose). Rats received gavage in a dosage of 5 mL/kg and each dose of the compound dissolved with CMCNa. After 20 min, the rats received gavage in a dosage of 30 mL/kg water. The study time interval of different doses of the same compound was over 24 hours.

Figure 4:
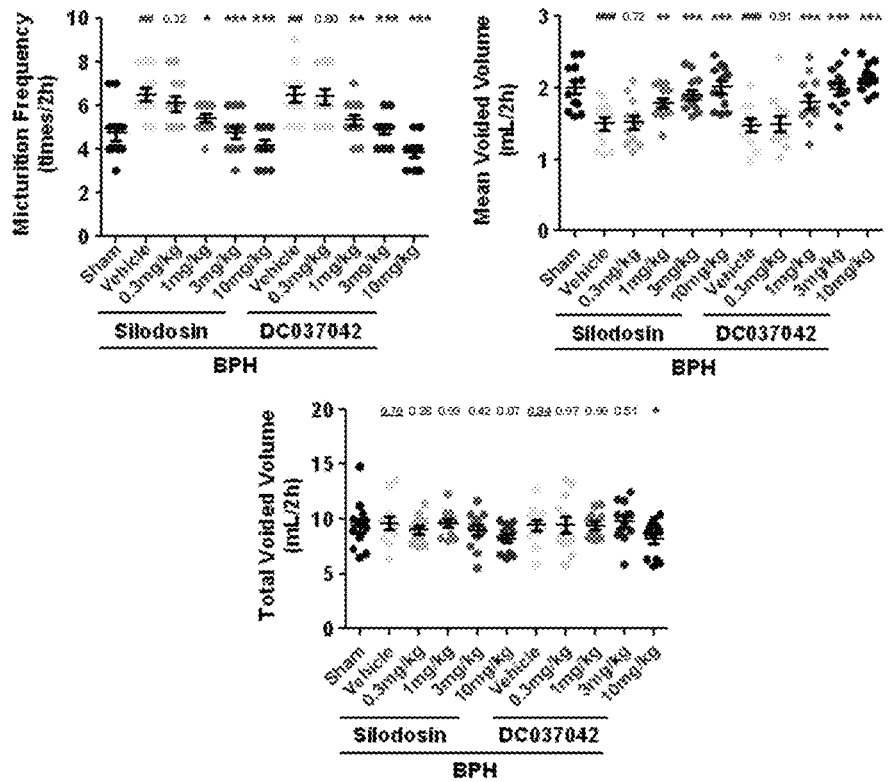
FIG. 4 shows micturition frequency, mean voided volume, total voided volume of rats in sham group, silodosin group (BPH-1,3 dosage group) and DC037009 group (BPH-2,3 dosage group) in Example 5 of invention.

The frequency of urination, single urine output of silodosin and DC037009 group rats all showed a dose-dependent relationship. DC037009 was comparable to the positive drug, and the onset dose was 1 mg/kg. Pharmacodynamic experiment proved that, under certain total urine output, compound DC037009 could significantly increase the single urine output and reduce frequency of urination (FIG. 4).

Example 6

Pharmacokinetics Study

Gavage administration to rats. 3 healthy SD rats (male, weighed 200-220 g) were fasted for 12 hours before the administration but were allowed to drink water. Compound DC037009 was formulated with 10% DMSO/10% Tween 80/80% saline and was administered by 20 mg/kg dose and the dosing volume was 10 mL/kg.

Intravenous administration to rats. 3 healthy SD rats (male, weighed 200-220 g) were fasted for 12 hours before the administration but were allowed to drink water. Compound DC037009 was formulated with 10% DMSO/10% Tween 80/80% saline and was administered via the rat tail vein injection by 10 mg/kg dose and the dosing volume was 5 mL/kg.

Gavage administration: 0.25, 0.5, 1.0, 2.0, 3.0, 5.0, 7.0, 9.0 and 24 h after administration;

Intravenous administration: 5 min, 0.25, 0.5, 1.0, 2.0, 3.0, 5.0, 7.0, 9.0 and 24 hrs after administration.

At the above time points, 0.3 mL blood obtained from post-eye venous plexus of rat was set into a heparinized tube, which was 11000 rpm centrifuged for 5 min, and the plasma was separated and frozen at −20° C. in a refrigerator.

After gavage administration to rats with 20 mg/kg DC037009, the time reaching peak plasma concentration in rats $T_{max}$ was 0.67±0.29 h, the peak concentration $C_{max}$ was 453±147 ng/mL, the plasma concentration-time area under the curve $AUC_{0-t}$ was 2867±798 ng·h/mL, and the elimination half-life $t_{1/2}$ was 3.26±0.82 h.

Figure 5:
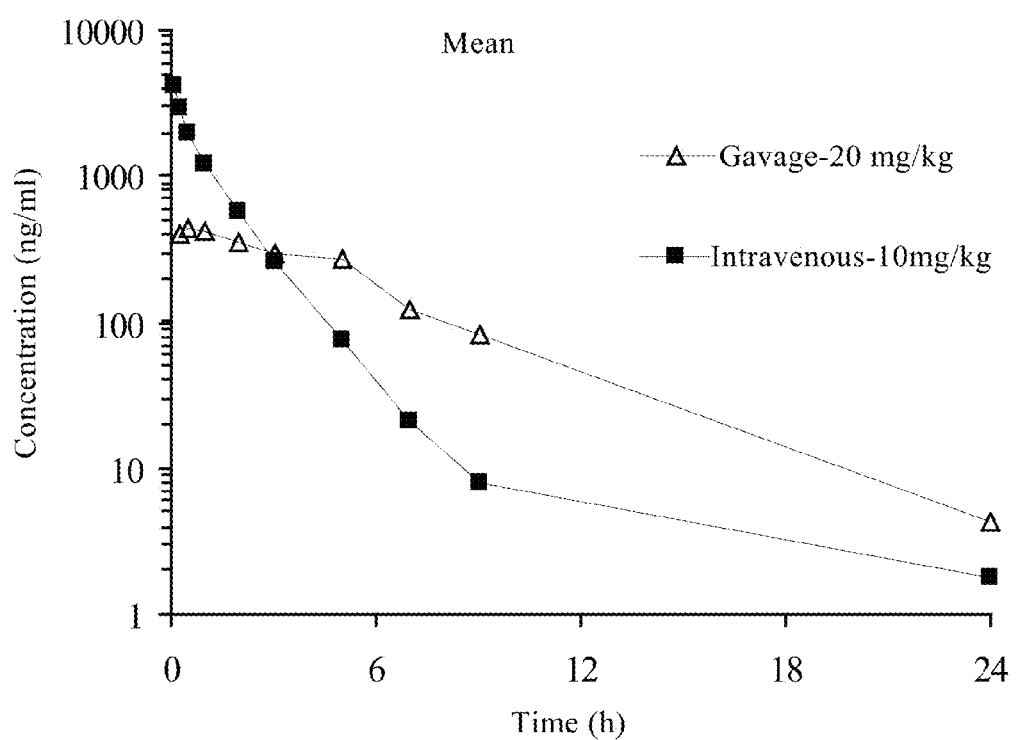
FIG. 5 shows a plasma concentration-time curve after intragastric administration and intravenous injection of DC037009 to rats in Example 6 of invention.

After administered 10 mg/kg DC037009 via intravenous injection, $AUC_{0-t}$ was 4196±141 ng·h/mL, $t_{1/2}$ was 5.44±0.85 h, plasma clearance rate CL was 2.38±0.08 L/h/kg, and volume distribution stead state Vss was 3.49±0.24 L/kg (see FIG. 5).

TABLE 4

Pharmacokinetic parameters after administrating 20 mg/kg DC037009 via gavage

| Animal No. | $T_{max}$ (h) | $C_{max}$ (ng/mL) | $AUC_{0-t}$ (ng · h/mL) | $AUC_{0-\infty}$ (ng · h/mL) | MRT (h) | $t_{1/2}$ (h) | F (%) |
|---|---|---|---|---|---|---|---|
| 1 | 0.50 | 494 | 2260 | 2265 | 4.00 | 2.89 | |
| 2 | 1.00 | 575 | 3771 | 3779 | 4.67 | 2.70 | |
| 3 | 0.50 | 289 | 2570 | 2629 | 6.45 | 4.20 | |
| Mean value | 0.67 | 453 | 2867 | 2891 | 5.04 | 3.26 | 34.2 |
| Standard | 0.29 | 147 | 798 | 790 | 1.27 | 0.82 | |
| CV (%) | 43.3 | 32.6 | 27.8 | 27.3 | 25.1 | 25.1 | |

As for bioavailability and half-life, the half-life and bioavailability of compound DC037009 in rats were 3.26 h and 34.2% respectively, and $AUC_{0-t}$ was 2260 ng·h/mL. The preliminary results of pharmacokinetics experiments showed that this class of compounds had better pharmacokinetic properties.

Example 7

In Vitro Comparative Study of DC037009 of Metabolism Between Different Species

The total volume of each incubation system was 200 μL, and the medium was 100 mM phosphate buffer solution (PBS, pH7.4) comprising a final concentration of 3 μM DC037009 and 2 mM NADPH. A 37° C. water bath was used for incubation. After 3 minutes of pre-incubation, various liver microsomes protein were added into the buffer-substrate-cofactors mixture to start reaction. The concentration of liver microsomal protein of various species was 1.0 mg/mL. After reacting 60 min, the reaction was terminated with isovolumetric ice-cold acetonitrile. The total volume of blank was 200 μL, and the medium was 100 mM phosphate buffer solution (PBS, pH 7.4), comprising a final concentration of 3 μM DC037009 and heat inactivated microsomal proteins. All incubation samples were double.

A 150 μL sample from each of double incubation samples was mixed. A 300 μL of acetonitrile was added, mixed by vortexing for 1 min, and centrifuged 5 min (11000 rpm). The supernatant was placed in a 10 mL tube, and dried in 40° C. with nitrogen stream. The residue was dissolved with 100 μL methanol/water (1:9, v/v). A 10 μL sample was taken for UPLC/Q-TOF MS analysis.

The metabolism of DC037009 in the monkey and mouse liver microsome was unstable, and only a small amount of prototype drug was detected. Metabolic stability in dog and rat liver microsome was in second place, and the metabolic stability in human liver microsome was relatively higher. After 60 min incubation, approximately 26% of prototype drug was metabolized. Four kinds of metabolites in human liver microsome were detected, seven kinds of metabolites were detected in monkey liver microsome, six kinds of metabolites were detected in dog liver microsome, eight kinds of metabolites were detected in rat liver microsome, and eight kinds of metabolite in mouse liver microsome were detected. The production of each of metabolites was NADPH dependent. The major metabolic pathway of DC037009 in human liver microsome was O-demethylation, dioxolane ring opening and dehydrogenation, and the relative proportions of metabolites generated showed that human and dog liver microsomes had good similarity.

In vitro results of metabolism difference of various species showed that although the metabolisms of compound DC037009 were unstable in monkey and mouse liver microsome cells, the types of metabolites in human liver microsome cell were obviously decreased, and the stability was greatly improved, and after 60 min incubation, only 26% of the prototype drug was metabolized. This further illustrated that DC037009 had good drug metabolic properties and had potential to become a medicine.

Example 8

Safety Evaluation

TABLE 6

Inhibition effect of DC037009 on hERG

| Compound | Maximum inhibition rate (%) | $IC_{50}$ (μM) |
|---|---|---|
| DC037009 | 84.7 | 8.1 |
| Dofetilide (Control) | 97.7 | 0.089 |

The antagonistic activity of DC037009 to $\alpha_{1A}$-receptor was 272 folds of its inhibitory activity on hERG, indicating that the compound had a weak inhibitory effect on heart, and it was less likely to produce side effects on heart.

TABLE 5

Metabolism information of DC037009 in liver microsomes from five species including human, monkey, dog, rat and mice.

| No. | Metabolic pathways | Mass-to-charge ratio | Formula | Retention time (min) | Human | monkey | dog | rat | mice |
|---|---|---|---|---|---|---|---|---|---|
| M0 | Prototype drug | 340.155 | $C_{20}H_{21}NO_4$ | 9.1 | 416.8 | 1.6 | 171.3 | 115.4 | 6.3 |
| M1 | Double O-demethylation and dehydrogenation | 310.108 | $C_{18}H_{15}NO_4$ | 8.3 | — | 30.8 | — | 13.3 | 24.0 |
| M2 | Double O-demethylation | 312.124 | $C_{18}H_{17}NO_4$ | 6.4 | — | 57.0 | 7.2 | 10.1 | 46.3 |
| M3 | Single-O-demethylation and dioxolane ring opening | 314.139 | $C_{18}H_{19}NO_4$ | 4.9 | — | 57.0 | 11.1 | 19.5 | 32.2 |
| M4 | Single-O-demethylation and continuous dehydrogenation | 322.105 | $C_{19}H_{15}NO_4$ | 10.1 | — | — | — | 12.0 | 12.0 |
| M5 | Single-O-demethylation and dehydrogenation | 324.124 | $C_{19}H_{17}NO_4$ | 9.2 | 26.5 | 23.7 | 45.3 | 43.3 | 30.6 |
| M6-1 | Single-O-demethylation | 326.139 | $C_{19}H_{19}NO_4$ | 7.3 | 10.8 | 9.6 | 65.8 | 30.1 | 32.0 |
| M6-2 | Single-O-demethylation | 326.139 | $C_{19}H_{19}NO_4$ | 8.1 | 18.0 | 3.2 | 11.4 | 73.5 | 21.0 |
| M7 | Dioxolane ring opening | 328.155 | $C_{19}H_{21}NO_4$ | 6.3 | 89.2 | 15.2 | 164.6 | 23.2 | 24.8 |

Effect of DC037009 on Seminal Vesicle Contraction Caused by Electrical Stimulation of Hypogastric Nerve in Normal Rats Experimental results showed that DC037009 had no significant inhibitive effect on contraction amplitude and area under contraction curve in rat seminal vesicle induced by electrical stimulation (P>0.05), indicating that the test compound did not act on the seminal vesicle of rats to affect its ejaculation function. This further proved that the side effect of this compound is possibly small.

Acute Toxicity Experiment of DC037009 on SD Rats by Oral Gavage

SD rats were administered compound DC037009 with single dose of 500 and 1000 mg/kg by oral gavage. No death rat was found and no obvious drug-related changes was seen after anatomy and the maximum tolerated dose (MTD) was 1000 mg/kg.

Repetitive Dose Toxicity Experiment of DC037009 on SD Rats for 14 Days

SD rats were orally administered with drug in a dosage of 0, 100 and 200 mg/kg for 14 days, and no death rat was found.

Compared with the excipient control group, the test result of blood and coagulation indicators and serum biochemical indicators in the animals given 100 and 200 mg/kg showed that the changes of blood and coagulation indicators and changes of serum biochemical indicators were not dose-dependent and in the laboratory normal range. Therefore, it did not show any toxicological significance. In gross anatomy, all animals showed no pathological changes related to administrated drug.

Acute toxicity and sub acute toxicity test results showed that the toxicity of compound DC037009 in rats was small, and it was safe and reliable. Meanwhile, compound DC037009 exhibited a large therapeutic window, indicating that the compound had great application value.

Example 9

Pharmaceutical Research of Compound DC037009

Solubility of Compound

TABLE 7

Solubility in different pH solution and pH changes of the solution

| Test sample | Solubility (1) (μg/mL) | Solubility (2) (μg/mL) | Dissolving capacity | pH value (1) | pH value (2) |
|---|---|---|---|---|---|
| pH = 1 | >1000 | >1000 | Slightly soluble | 1.09 | 1.03 |
| pH = 2 | >1000 | >1000 | Slightly soluble | 2.02 | 2.07 |
| pH = 4 | 400.51 | 402.68 | Slightly soluble | 5.02 | 5.10 |
| pH = 6 | 46.01 | 50.16 | Sparingly soluble | 6.11 | 6.14 |
| pH = 8 | <10 | <10 | Sparingly soluble | 8.06 | 8.07 |

The solubility in acidic solution was greater than that in alkaline solution, and pH of solution would increase after adding compound DC037009.

Stability of the Compound and pKa Determination:

Compound DC037009 was heated at 80° C. for 24 hours, and the compound purity only varied 0.5%. The pKa of the compound in different solvents were pKa ($H_2O$)=7.28, and pKa ($CH_3OH$)=6.81.

The above pharmacy data indicated that compound DC037009 had basic nature to become a medicine and had potential applications.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A method of treating benign prostatic hyperplasia diseases, the method comprising administering to a subject in need thereof a therapeutically effective amount of a chiral hexahydrodibenzo[a,g]quinolizine compound of formula (I), or a pharmaceutically acceptable salt, solvate, stereoisomer, or tautomer thereof:

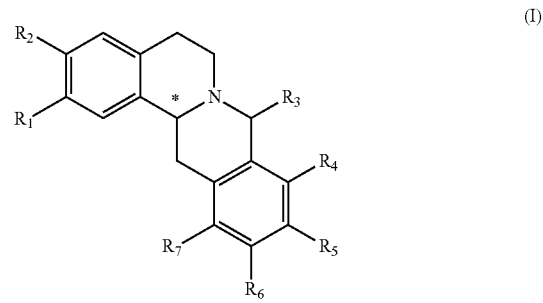

wherein
$R_3$ is hydrogen or an unsubstituted C1-C6 alky;
each of $R_1$, $R_2$, $R_4$, $R_5$, $R_6$ and $R_7$ is independently hydrogen, hydroxy, halogen, a substituted or unsubstituted C1-C6 alkoxy, a substituted or unsubstituted C1-C6 alkyl, a substituted or unsubstituted C2-C6 alkenyl, a substituted or unsubstituted C2-C6 alkynyl, a substituted or unsubstituted C3-C6 cycloalkyl, or a substituted or unsubstituted benzyloxy wherein a substituent for substitution is halogen, hydroxy, amino or sulfonyl;
optionally, $R_1$ and $R_2$ together form a substituted or unsubstituted 5-7 membered heterocycle, wherein a substituent for substitution is halogen or an unsubstituted or halogen-substituted C1-C6 alkyl, and said heterocycle contains 1-3 heteroatoms selected from the group consisting of N, O, and S;
optionally, any two adjacent substituents of $R_4$, $R_5$, $R_6$ and $R_7$ together form a substituted or unsubstituted 5-7 membered heterocycle, wherein a substituent for substitution is halogen, an unsubstituted or halogen-substituted C1-C6 alkyl or an unsubstituted or halogen-substituted C1-C6 alkoxy, and said heterocycle contains 1-3 heteroatoms selected from the group consisting of N, O, and S;
provided at least one substituted or unsubstituted 5-7 membered heterocycle is formed by $R_1$ and $R_2$ together or an two adjacent substituents of $R_4$, $R_5$, $R_6$ and $R_7$, and
the configuration of the chiral carbon atom labeled "*" in the compound of general formula (I) is either R or S.

2. The method of claim 1, wherein
$R_3$ is hydrogen;
each of $R_4$, $R_5$, $R_6$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, or a substituted or unsubstituted benzyloxy, wherein a substituent for substitution is halogen, hydroxy, amino or sulfonyl;

$R_1$ and $R_2$ together form a substituted or unsubstituted 5-7 membered heterocycle, wherein a substituent for substitution is halogen or unsubstituted or halogen-substituted C1-C4 alkyl, and said heterocycle contains 1-3 heteroatoms selected from the group consisting of N, O, and S;

or, each of $R_1$, $R_2$, $R_4$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, a substituted or unsubstituted benzyloxy, wherein a substituent for substitution is halogen, hydroxy , amino or sulfonyl; and $R_5$ and $R_6$ together form a substituted or unsubstituted 5-7 membered heterocycle, wherein a substituent for substitution is halogen, an unsubstituted or halogen-substituted C1-C4 alkyl or an unsubstituted or halogen-substituted C1-C4 alkoxy, and said heterocycle contains 1-3 heteroatoms selected from the group consisting of N, O, and S; and the configuration of the chiral carbon atom labeled "*" in the compound of general formula (I) is either R or S.

3. The method of claim 1, wherein, $R_3$ is hydrogen;

each of $R_4$, $R_5$, $R_6$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen, hydroxy, or an amino;

$R_1$ and $R_2$ together form a substituted or unsubstituted 5 or 6 membered heterocycle, wherein a substituent for substitution is halogen or an unsubstituted or halogen-substituted C1-C4 alkyl, and said heterocycle contains 1-3 heteroatoms selected from the group consisting of N, O, and S;

or, each of $R_1$ $R_2$ $R_4$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen, hydroxy , or an amino; and $R_5$ and $R_6$ together form a substituted or unsubstituted 5 or 6 membered heterocycle, wherein a substituent for substitution is halogen, an unsubstituted or halogen-substituted C1-C4 alkyl or an unsubstituted or halogen-substituted C1-C4 alkoxy, and said heterocycle contains 1-3 heteroatoms selected from the group consisting of N, O, and S; and the configuration of the chiral carbon atom labeled "*" in the compound of general formula (I) is either R or S.

4. The method of claim 1, wherein $R_3$ is hydrogen;

each of $R_4$, $R_5$, $R_6$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen or hydroxy;

$R_1$ and $R_2$ together form a 5 or 6 membered heterocycle which contains 1 to 2 heteroatoms selected from the group consisting of N, O, and S;

or, each of $R_1$, $R_2$, $R_4$ and $R_7$ is independently hydrogen, hydroxy, halogen, a substituted or unsubstituted C1-C4 alkoxy, a substituted or unsubstituted C1-C4 alkyl, or a substituted or unsubstituted benzyloxy, wherein a substituent for substitution is halogen or hydroxy; and $R_5$ and $R_6$ together form a 5 or 6 membered heterocycle which contains 1 to 2 heteroatoms selected from the group consisting of N, O, and S; and the configuration of the chiral carbon atom labeled "*" in the compound of general formula (I) is either R or S.

5. The method of claim 1, wherein the chiral hexahydrodibenzo[a,g]quinolizine compound of formula (I) is selected from the group consisting of:

| NO. | Structure |
|---|---|
| DC037007 | 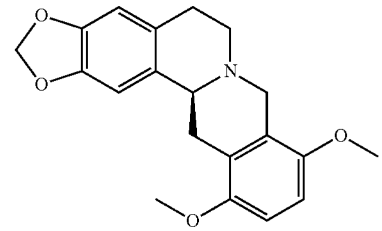 [SMILES: COc1ccc(OC)c2c1C[C@H]1c3cc4c(cc3CCN1C2)OCO4] |
| DC037009 | 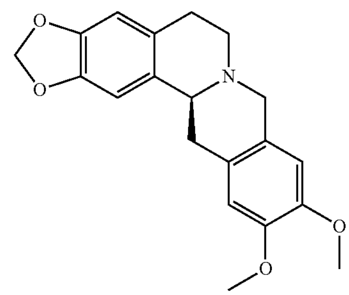 [SMILES: COc1cc2c(cc1OC)CN1CCc3cc4c(cc3[C@@H]1C2)OCO4] |
| DC037010 | 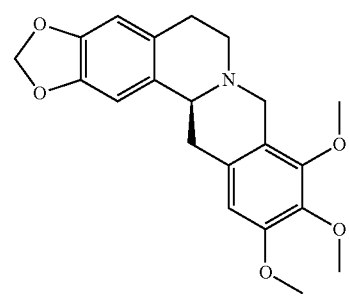 [SMILES: COc1cc2c(c(OC)c1OC)CN1CCc3cc4c(cc3[C@@H]1C2)OCO4] |
| DC037005 | 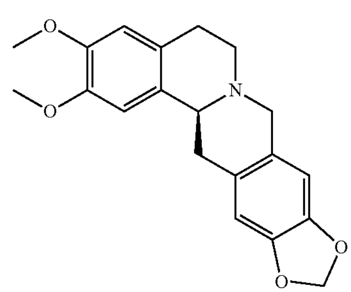 [SMILES: COc1cc2c(cc1OC)[C@@H]1Cc3cc4c(cc3CN1CC2)OCO4] |

| NO. | Structure |
|---|---|
| DC037006 | 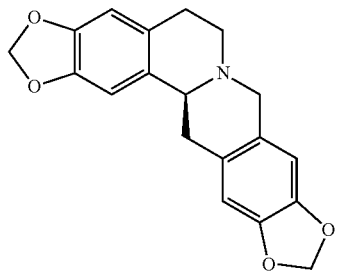 |
| DC037013 | 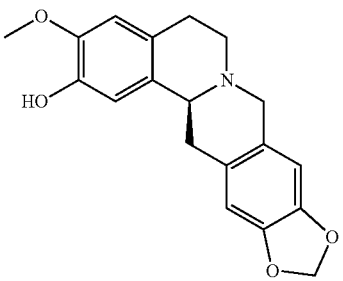 [SMILES: COc1cc2c(cc1O)[C@@H]1Cc3cc4c(cc3CN1CC2)OCO4] |
| DC037019 | 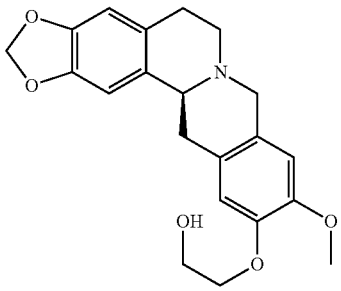 |
| DC037014 | 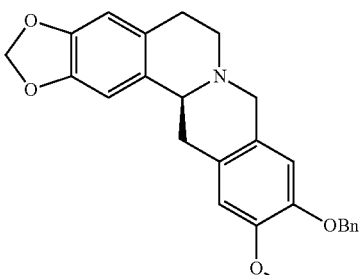 |
| DC037020 | 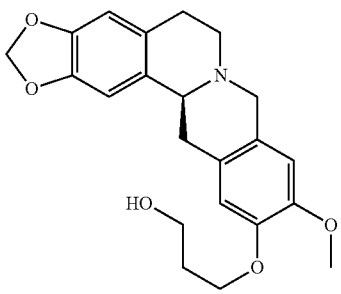 [SMILES: COc1cc2c(cc1OCCCO)C[C@H]1c3cc4c(cc3CCN1C2)OCO4] |
| NO. | Structure |
|---|---|
| DC037015 | 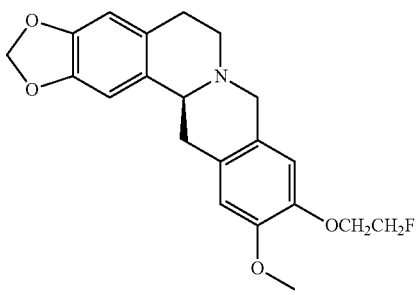 |
| DC037021 | 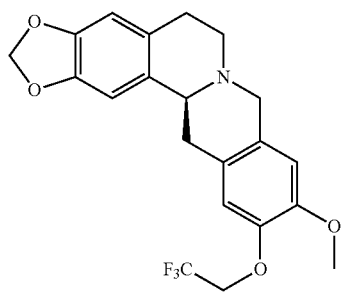 [SMILES: COc1cc2c(cc1OCC(F)(F)F)C[C@H]1c3cc4c(cc3CCN1C2)OCO4] |
| DC037016 | 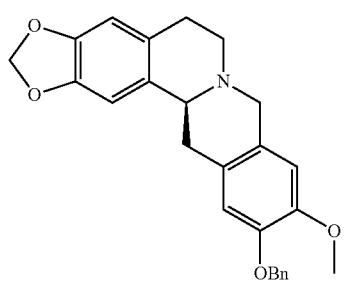 |
| DC037022 | 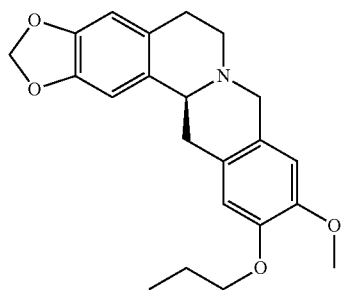 [SMILES: CCCOc1cc2c(cc1OC)CN1CCc3cc4c(cc3[C@@H]1C2)OCO4] |
| DC037017 | 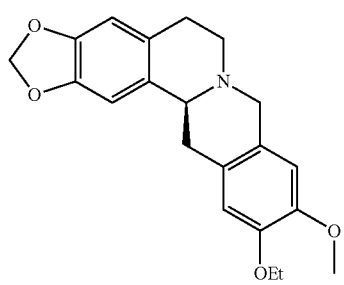 |

| NO. | Structure |
|---|---|
| DC037023 | 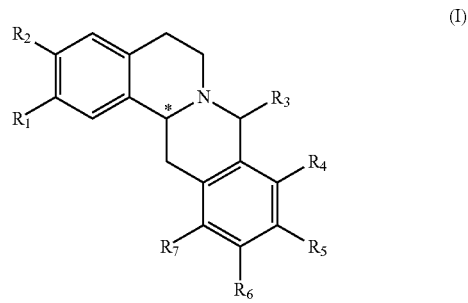 and |
| DC037018 | 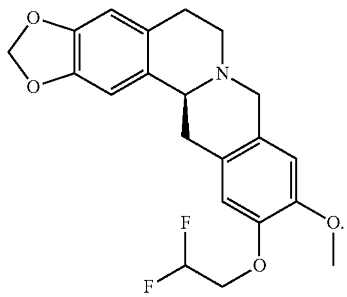 [SMILES: COc1cc2c(cc1OCC(F)F)C[C@H]1c3cc4c(cc3CCN1C2)OCO4] |

6. The method of claim 1, wherein the chiral hexahydrodibenzo[a,g]quinolizine compound of formula (I) selectively binds to an $\alpha_{1A}$ adrenergic receptor.

7. The method of claim 1, wherein the chiral hexahydrodibenzo[a,g]quinolizine compound of formula (I) selectively inhibits contraction of urinary system smooth muscle.

8. A method of selectively inhibiting an $a_{1A}$-adrenergic receptor comprising contacting the $\alpha_{1A}$-adrenergic receptor with a chiral hexahydrodibenzo[a,g]quinolizine compound of formula (I) or a pharmaceutically acceptable salt, solvate, stereoisomer, or tautomer thereof:

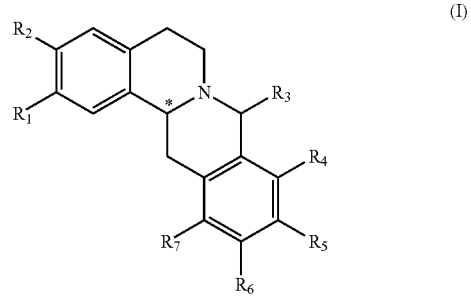

(I)

wherein
$R_3$ is hydrogen or an unsubstituted C1-C6 alky;
each of $R_1$, $R_2$, $R_4$, $R_5$, $R_6$ and $R_7$ is independently hydrogen, hydroxy, halogen, a substituted or unsubstituted C1-C6 alkoxy, a substituted or unsubstituted C1-C6 alkyl, a substituted or unsubstituted C2-C6 alkenyl, a substituted or unsubstituted C2-C6 alkynyl, a substituted or unsubstituted C3-C6 cycloalkyl, or a substituted or unsubstituted benzyloxy, wherein a substituent for substitution is halogen, hydroxy, amino or sulfonyl;
optionally, $R_1$ and $R_2$ together form a substituted or unsubstituted 5-7 membered heterocycle, wherein a substituent for substitution is halogen or an unsubstituted or halogen-substituted C1-C6 alkyl, and said heterocycle contains 1-3 heteroatoms selected from the group consisting of N, O, and S;
optionally, any two adjacent substituents of $R_4$, $R_5$, $R_6$ and $R_7$ together form a substituted or unsubstituted 5-7 membered heterocycle, wherein a substituent for substitution is halogen, an unsubstituted or halogen-substituted C1-C6 alkyl or an unsubstituted or halogen-substituted C1-C6 alkoxy, and said heterocycle contains 1-3 heteroatoms selected from the group consisting of N, O, and S;
provided at least one substituted or unsubstituted 5-7 membered heterocycle is formed by $R_1$ and $R_2$ together, or any two adjacent substituents of $R_4$, $R_5$, $R_6$ and $R_7$, and
the configuration of the chiral carbon atom labeled "*" in the compound of formula (I) is either R or S.

9. A method for antagonizing norepinephrine-induced contraction of urethra smooth muscle or prostatic smooth muscle, the method comprising administering to a subject in need thereof an effective amount of a chiral hexahydrodibenzo[a,g]quinolizine compound of formula (I) or a pharmaceutically acceptable salt, solvate, stereoisomer, or tautomer thereof:

(I)

wherein
$R_3$ is hydrogen or an unsubstituted C1-C6 alkyl;
each of $R_1$, $R_2$, $R_4$, $R_5$, $R_6$ and $R_7$ is independently hydrogen, hydroxy, halogen, a substituted or unsubstituted C1-C6 alkoxy, a substituted or unsubstituted C1-C6 alkyl, a substituted or unsubstituted C2-C6 alkenyl, a substituted or unsubstituted C2-C6alkynyl, a substituted or unsubstituted C3-C6 cycloalkyl, or a substituted or unsubstituted benzyloxy, wherein a substituent for substitution is halogen, hydroxy, amino or sulfonyl;
optionally, $R_1$ and $R_2$ together form a substituted or unsubstituted 5-7 membered heterocycle, wherein a substituent for substitution is halogen or an unsubstituted or halogen-substituted C1-C6 alkyl, and said heterocycle contains 1-3 heteroatoms selected from the group consisting of N, O, and S;
optionally, any two adjacent substituents of $R_4$, $R_5$, $R_6$ and $R_7$ can together form a substituted or unsubstituted 5-7 membered heterocycle, wherein a substituent for substitution is halogen, an unsubstituted or halogen-substituted C1-C6 alkyl or an unsubstituted or halogen-substituted C1-C6 alkoxy, and said heterocycle contains 1-3 heteroatoms selected from the group consisting of N, O, and S;

provided at least one substituted or unsubstituted 5-7 membered heterocycle is formed by $R_1$ and $R_2$ together, or any two adjacent substituents of $R_4$, $R_5$, $R_6$ and $R_7$, and the configuration of the chiral carbon atom labeled "*" in the compound of formula (I) is either R or S.

10. The method according to claim 8, wherein $R_3$ is hydrogen;

each of $R_4$, $R_5$, $R_6$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, or a substituted or unsubstituted benzyloxy, wherein a substituent for substitution is halogen, hydroxy, amino or sulfonyl;

$R_1$ and $R_2$ together form a substituted or unsubstituted 5-7 membered heterocycle, wherein a substituent for substitution is halogen or unsubstituted or halogen-substituted C1-C4 alkyl, and said heterocycle contains 1-3 heteroatoms selected from the group consisting of N, O, and S;

or, each of $R_1$, $R_2$, $R_4$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, a substituted or unsubstituted benzyloxy, wherein a substituent for substitution is halogen, hydroxy, amino or sulfonyl; and $R_5$ and $R_6$ together form a substituted or unsubstituted 5-7 membered heterocycle, wherein a substituent for substitution is halogen, an unsubstituted or halogen-substituted C1-C4 alkyl or an unsubstituted or halogen-substituted C1-C4 alkoxy, and said heterocycle contains 1-3 heteroatoms selected from the group consisting of N, O, and S; and the configuration of the chiral carbon atom labeled "*" in the compound of general formula (I) is either R or S.

11. The method according to claim 8, wherein the chiral hexahydrodibenzo[a,g]quinolizine compound of formula (I) is selected from the group consisting of:

| NO. | Structure |
|---|---|
| DC037007 | 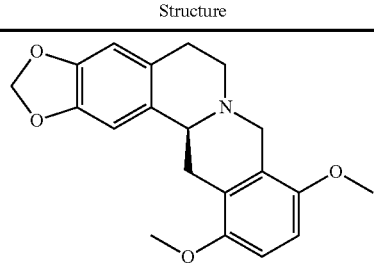 |
| DC037009 | 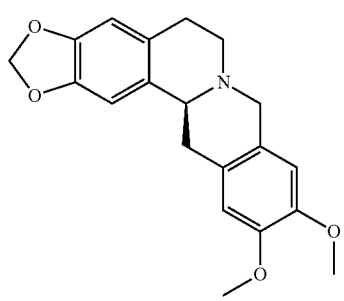 [SMILES: COc1cc2c(cc1OC)CN1CCc3cc4c(cc3[C@@H]1C2)OCO4] |
| DC037010 | 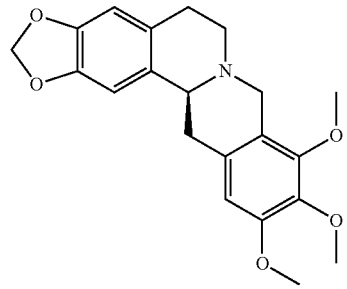 [SMILES: COc1cc2c(c(OC)c1OC)CN1CCc3cc4c(cc3[C@@H]1C2)OCO4] |
| DC037005 | 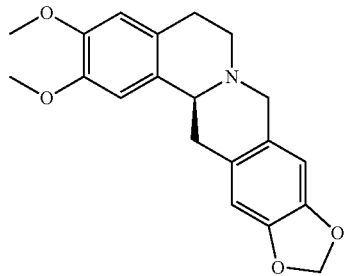 [SMILES: COc1cc2c(cc1OC)[C@@H]1Cc3cc4c(cc3CN1CC2)OCO4] |
| DC037006 | 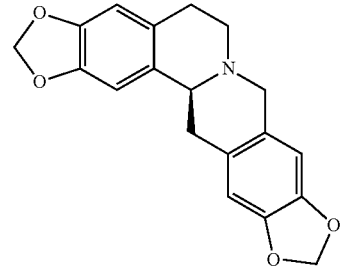 |
| DC037013 | 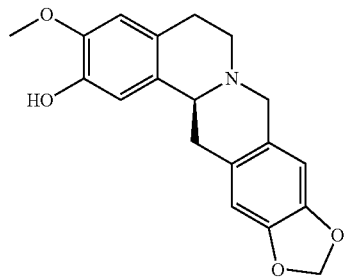 |
| DC037019 | 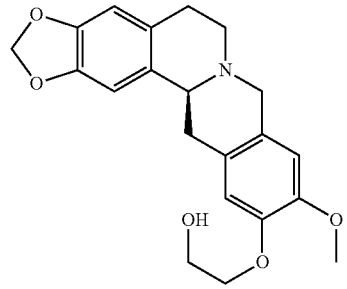 |

| NO. | Structure |
|---|---|
| DC037014 | 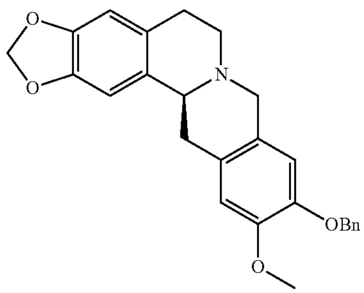 [SMILES: COc1cc2c(cc1OCc1ccccc1)CN1CCc3cc4c(cc3[C@@H]1C2)OCO4] |
| DC037020 | 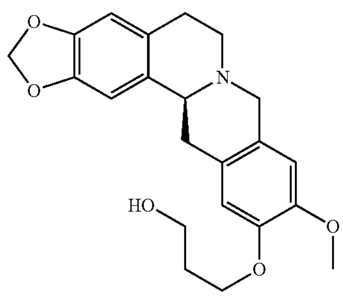 [SMILES: COc1cc2c(cc1OCCCO)C[C@H]1c3cc4c(cc3CCN1C2)OCO4] |
| DC037015 | 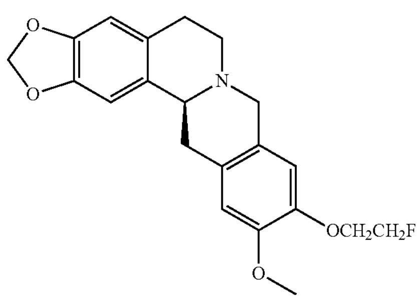 |
| DC037021 | 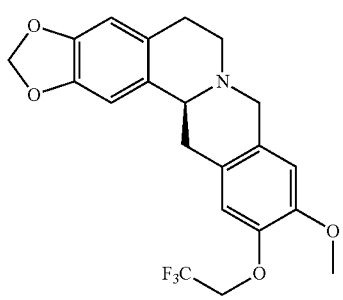 [SMILES: COc1cc2c(cc1OCC(F)(F)F)C[C@H]1c3cc4c(cc3CCN1C2)OCO4] |
| DC037016 | 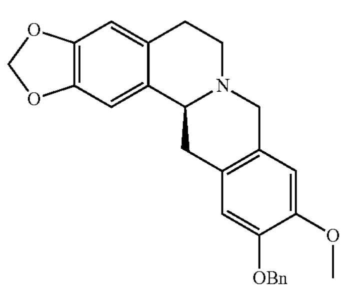 |

| NO. | Structure |
|---|---|
| DC037022 | |
| DC037017 | |
| DC037023 | and |
| DC037018 | |

12. The method according to claim 9, wherein
R$_3$ is hydrogen;
each of R$_4$, R$_5$, R$_6$ and R$_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, or a substituted or unsubstituted benzyloxy, wherein a substituent for substitution is halogen, hydroxy, amino or sulfonyl;
R$_1$ and R$_2$ together form a substituted or unsubstituted 5-7 membered heterocycle, wherein a substituent for substitution is halogen or unsubstituted or halogen-substituted C1-C4 alkyl, and said heterocycle contains 1-3 heteroatoms selected from the group consisting of N, O, and S;

or, each of $R_1$, $R_2$, $R_4$ and $R_7$ is independently hydrogen, hydroxy, halogen, a substituted or unsubstituted C1-C4 alkoxy, a substituted or unsubstituted C1-C4 alkyl, a substituted or unsubstituted C2-C4 alkenyl, a substituted or unsubstituted C2-C4 alkynyl, a substituted or unsubstituted C3-C6 cycloalkyl, a substituted or unsubstituted benzyloxy, wherein a substituent for substitution is halogen, hydroxy, amino or sulfonyl; and $R_5$ and $R_6$ together form a substituted or unsubstituted 5-7 membered heterocycle, wherein a substituent for substitution is halogen, an unsubstituted or halogen-substituted C1-C4 alkyl or an unsubstituted or halogen-substituted C1-C4 alkoxy, and said heterocycle contains 1-3 heteroatoms selected from the group consisting of N, O, and S; and the configuration of the chiral carbon atom labeled "*" in the compound of general formula (I) is either R or S.

13. The method according to claim 9, wherein the chiral hexahydrodibenzo[a,g]quinolizine compound of formula (I) is selected from the group consisting of:

| NO. | Structure |
|---|---|
| DC037007 | |
| DC037009 | |
| DC037010 | |
| DC037005 | 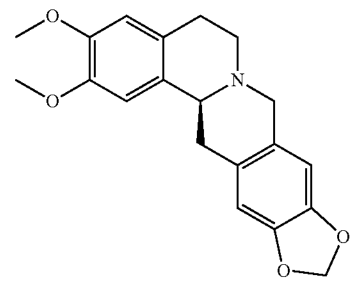 [SMILES: COc1cc2c(cc1OC)[C@@H]1Cc3cc4c(cc3CN1CC2)OCO4] |
| DC037006 | 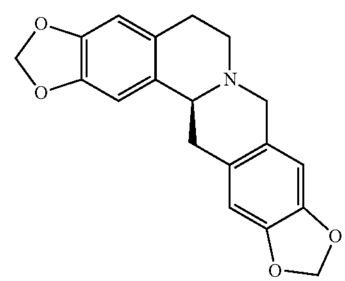 [SMILES: c1c2c(cc3c1OCO3)CN1CCc3cc4c(cc3[C@@H]1C2)OCO4] |
| DC037013 | 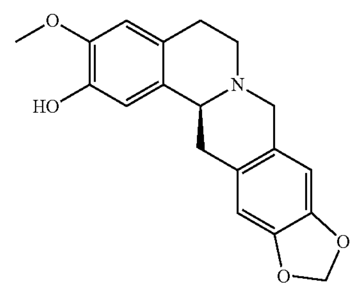 [SMILES: COc1cc2c(cc1O)[C@@H]1Cc3cc4c(cc3CN1CC2)OCO4] |
| DC037019 | 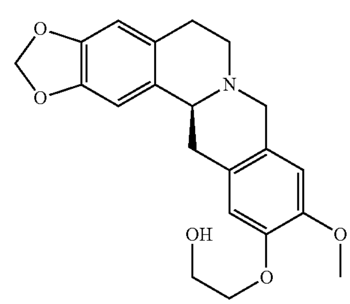 |
| DC037014 | 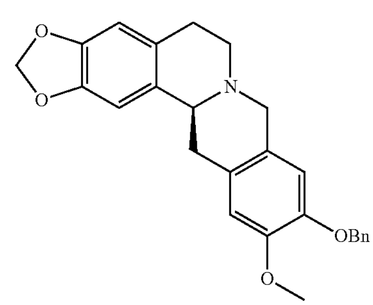 [SMILES: COc1cc2c(cc1OCc1ccccc1)CN1CCc3cc4c(cc3[C@@H]1C2)OCO4] |

| NO. | Structure |
|---|---|
| DC037020 | 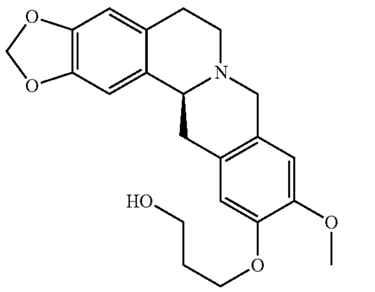 [SMILES: COc1cc2c(cc1OCCCO)C[C@H]1c3cc4c(cc3CCN1C2)OCO4] |
| DC037015 | 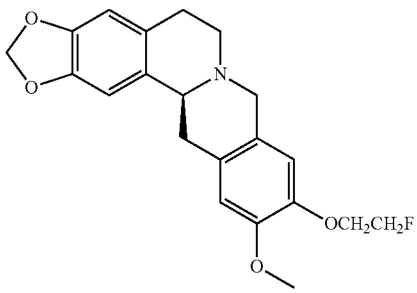 |
| DC037021 | 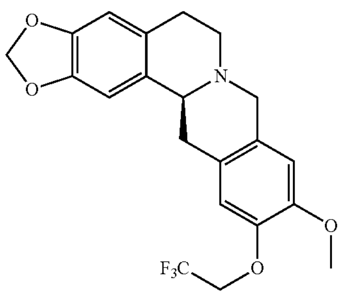 [SMILES: COc1cc2c(cc1OCC(F)(F)F)C[C@H]1c3cc4c(cc3CCN1C2)OCO4] |
| DC037016 | 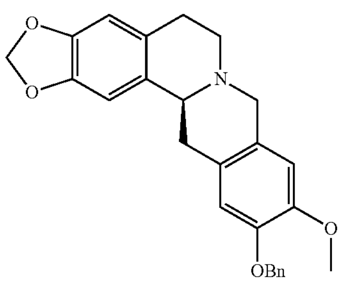 |

| NO. | Structure |
|---|---|
| DC037022 | |
| DC037017 | |
| DC037023 | and |
| DC037018 | |

* * * * *